United States Patent
Bansal et al.

(10) Patent No.: US 10,842,959 B2
(45) Date of Patent: Nov. 24, 2020

(54) FOOT PEDAL

(71) Applicant: SECRETARY, DEPARTMENT OF BIOTECHNOLOGY, New Delhi (IN)

(72) Inventors: Avijit Bansal, Uttar Pradesh (IN); Ayesha Chaudhary, Haryana (IN); Dinesh Kumar, New Delhi (IN); Sahaj Ghose, Orissa (IN); Amit Kumar, Uttar Pradesh (IN)

(73) Assignee: SECRETARY, DEPARTMENT OF BIOTECHNOLOGY, New Delhi (IN)

( * ) Notice: Subject to any disclaimer, the term of this patent is extended or adjusted under 35 U.S.C. 154(b) by 186 days.

(21) Appl. No.: 16/060,738

(22) PCT Filed: Dec. 9, 2016

(86) PCT No.: PCT/IB2016/001746
§ 371 (c)(1),
(2) Date: Jun. 8, 2018

(87) PCT Pub. No.: WO2017/098317
PCT Pub. Date: Jun. 15, 2017

(65) Prior Publication Data
US 2018/0369524 A1 Dec. 27, 2018

(30) Foreign Application Priority Data
Dec. 10, 2015 (IN) .......................... 4049/DEL/2015

(51) Int. Cl.
*A61M 16/00* (2006.01)
*A61M 16/12* (2006.01)
(Continued)

(52) U.S. Cl.
CPC ...... *A61M 16/022* (2017.08); *A61M 16/0009* (2014.02); *A61M 16/0051* (2013.01);
(Continued)

(58) Field of Classification Search
CPC .............. A61M 16/00; A61M 16/0009; A61M 16/0051; A61M 16/0057; A61M 16/0075;
(Continued)

(56) References Cited

U.S. PATENT DOCUMENTS

| 527,248 | A | * | 10/1894 | North | B60T 13/563 92/48 |
|---|---|---|---|---|---|
| 4,898,167 | A | * | 2/1990 | Pierce | A61M 16/0075 128/205.11 |
| 2010/0263670 | A1 | * | 10/2010 | Pearce | A61M 16/0075 128/205.14 |

FOREIGN PATENT DOCUMENTS

| CN | 203647820 U | 6/2014 |
|---|---|---|
| DE | 102014223396 A1 | 5/2016 |
| IN | 2012DE1814 A * | 6/2014 |

OTHER PUBLICATIONS

Your Story, "5 out of 100 babies won't breathe at birth: Startup Windmill alleviates the situation", retrieved from https://web.archive.org/web/20140821190400/http://yourstory.com//2013/05/5-out-of-100-babies-wont-breathe-at-birth-startup-windmill-alleviates-the-situation-2 with date Aug. 21, 2014.*
(Continued)

*Primary Examiner* — Joseph D. Boecker
(74) *Attorney, Agent, or Firm* — Rothwell, Figg, Ernst & Manbeck, P.C.

(57) ABSTRACT

The invention relates to an ergonomic foot pedal and to apparatuses for manual ventilation. In an embodiment, the invention provides a compact and integrated foot pedal that enables a care provider to provide positive pressure ventilation to a subject's airways and lungs, and to optionally apply suction for the purpose of aspirating mucous, secretions, meconium, blood, fluids or other such materials from a patient—specifically from airways.

15 Claims, 15 Drawing Sheets

(51) Int. Cl.
*A61M 16/20* (2006.01)
*A61M 16/08* (2006.01)

(52) U.S. Cl.
CPC .... *A61M 16/0075* (2013.01); *A61M 16/0078* (2013.01); *A61M 16/021* (2017.08); *A61M 16/0084* (2014.02); *A61M 16/0866* (2014.02); *A61M 16/0875* (2013.01); *A61M 16/12* (2013.01); *A61M 16/208* (2013.01); *A61M 16/209* (2014.02); *A61M 2016/003* (2013.01); *A61M 2016/0027* (2013.01); *A61M 2205/078* (2013.01)

(58) Field of Classification Search
CPC .......... A61M 16/0078; A61M 16/0084; A61M 16/021; A61M 16/022; A61M 2205/078
See application file for complete search history.

(56) References Cited

OTHER PUBLICATIONS

International Search Report and Written Opinion issued for International Application No. PCT/IB2016/001746 dated Mar. 24, 2017, 12 pages.

\* cited by examiner

FOOT PEDAL

CROSS REFERENCE TO RELATED APPLICATION(S)

The present application is a 35 U.S.C. § 371 National Phase Entry Application from PCT/IB2016/001746, filed on Dec. 9, 2016, which claims the benefits of priority to Indian Patent Application No. 4049/DEL/2015, filed Dec. 10, 2015, which are incorporated herein by reference in their entireties for all purposes.

FIELD OF THE INVENTION

The invention relates to an apparatus for manual positive pressure ventilation (including for example for resuscitation). In particular, the invention comprises an apparatus capable of providing ventilation and suction to a subject's airway.

BACKGROUND

Ventilation or resuscitation is the process of providing external assistance to enable or restore respiration in a subject suffering from respiratory impairment i.e. who is unable to maintain adequate respiration either due to an impairment of the respiratory system or any other system or a generalized condition. Ventilation comprises delivery of a mixture of gases containing air and/or other gases (such as oxygen or medical gases) under appropriate pressure through a subject's airway to the lungs, to inflate the lungs and allow adequate gas exchange, to maintain the subject's metabolism.

Delivery of air (inspiration) is spaced by appropriate intervals during which, previously delivered air is allowed to escape the lungs (expiration) by the lungs' own elastic recoil. In addition, to ensure that a subject's airways or air passages are clear to enable delivery of sufficient quantities of air, or for other purposes such as prevention of aspiration of undesirable materials (for example, meconium in neonates) it may become necessary to clear the airway of fluids or accumulated secretions. Introducing a thin conduit with negative pressure into a subject's airway is known to assist in clearing fluids and secretions to clear the airway for inspiration.

Prior art devices for manual ventilation are known. FIG. 1 illustrates a prior art ventilation device 100 comprising an air reservoir 102, a face mask 104 and a conduit 106 connecting air reservoir 102 and face mask 104, and providing a fluid passageway there between. The device may additionally include one or more valves for ensuring that air exhaled from the subject's lungs does not re-enter either or both of conduit 106 or air reservoir 102.

In the device illustrated in FIG. 1, air reservoir 102 comprises a squeezable bag, which deforms in response to external forces F, and drives air through conduit 106 and face mask 104 into a subject's airway (inspiration phase). Air reservoir 102 is typically self-inflating, in that it may be manufactured to have resilient or self-expanding properties that ensure air reservoir 102 regains its expanded configuration upon termination of compressive forces F.

In regaining its expanded configuration, air reservoir 102 draws air through air inlet 108 and replenishes its reservoir of air (restoration phase), in advance of the next inspiration phase. Air inlet 108 may be provided with a one way valve arrangement that enables air to be drawn into air reservoir 102 through air inlet 108, but which does not permit air to be driven back out through air inlet 108 in response to deformation of said air reservoir.

Facemask 104 provides an interface with a subject's airway and forms a seal about the patient's nose and mouth. The facemask may be made of a pliant material and is flexible so as to conform to and provide a sealing fit despite variations in facial anatomy. Ordinarily, face mask 104 must provide sufficient rigidity to enable formation of an airtight seal against a subject's facial anatomy—thereby preventing air from escaping during the inspiration phase.

The device illustrated in FIG. 1 enables health care providers to administer ventilation to a subject, and to control intervals, quantity and/or pressure of air delivered to the subject, by varying timing of the inspiration phase and/or force applied to the air reservoir.

FIG. 2 illustrates a prior art suction device 200 that is typically used to clear airway passages of mucus or accumulated secretions. Suction device 200 comprises a catheter tube 204 having a first end 204a and a second end 204b, and a suction tube 206 having a first end 206a and a second end 206b. The respective second ends 204b and 206b of the catheter tube 204 and the suction tube 206 are disposed within a mucous trap 202 and enter said mucous trap 202 through cap 208. The portion of suction tube 206 within mucous trap 202 is short and terminates relatively close to cap 208 and away from bottom end 210, while the portion of catheter tube 204 within mucous trap 202 is longer and terminates relatively further away from cap 208 and closer to bottom end 210.

In use, first end 204a of catheter tube 204 may be inserted into nasal passages, mouth or throat of a subject to clear the respiratory passages, while a care provider aspirates (draws air) through first end 206a of suction tube 206. This arrangement ensures that mucous is drawn through catheter tube 204, enters mucous trap 202 and remains at the bottom of trap 202, and that the mucous is not accidentally drawn from mucous trap 202 into suction tube 206 by the user.

The above described prior art devices suffer from multiple drawbacks.

A first potential drawback is observed in connection with use of ventilation device 100, where continuous application of compressive forces to air reservoir 102 may cause the operator to tire from having to continually squeeze the air reservoir by hand.

Additionally, at least one of the operator's hands is required for compressing air reservoir 102, leaving only one hand free for applying the face mask to a subject's facial anatomy. The inability to use more than one hand often causes an ineffective seal to be formed between face mask 104 and a subject's facial anatomy, resulting in air leakage and ineffective resuscitation.

Additionally, reliance on separate devices for ventilation and suction presents challenges in terms of storage, sanitation and convenience—particularly for mobile health care providers, or in emergency health care situations.

The most important drawback in prior art is that one of the operator(s) hands is required for the task of compressing the air reservoir, which leaves only one hand available for the task of applying the airway interface device (e.g. a mask) firmly to the patient's airway, for instance at the mouth and nose. Often a firm pressure is required to be applied for creation of an effective seal and this leads to quick tiring of the hand that is holding the mask. In addition, with the hand that is holding the mask, the operator also needs to perform what is known as the triple manoeuvre consisting of chin lift, neck tilt and jaw thrust. This triple manoeuvre also requires significant amount of force leading to quick tiring and ineffective sealing. Such ineffective sealing leads to leakage and consequently to inadequate volume delivery, underventilation and consequent ill-effects or continued hypoxia including death.

In addition, the air reservoir is an active component where force needs to be repeatedly applied at a high frequency throughout the procedure, mostly using fingers of one hand on one side and the thumb of the same hand on the other side. Since in prior art devices the dynamic air reservoir component and stable airway interface component are connected by a small rigid conduit, unbalanced, and constantly varying forces are often transmitted to the airway interface—which causes destabilization, lack of effective sealing and air leakage.

Irrespective of the nature of the resuscitation apparatus used (e.g. self inflating bag-mask, flow inflating bag-mask, T-piece resuscitator or any other type of resuscitation device) and the suction apparatus used (centralized suction through pipeline, electrically operated suction foot operated suction, bulb suction or mouth operated suction as shown in FIG. 2) all prior art devices describe resuscitation and suction devices as 2 independent devices. Independent devices for suction and ventilation creates several drawbacks, including the following:

Separate devices lead to situations where one of the respiration device or suction device is unavailable. There is accordingly a need for an integrated ventilation and suction device.

In the critical time period of less than a minute that is available for salvaging a patient, several valuable seconds may be lost in switching between two independent devices. An integrated device may eliminate the time lost in switching between devices.

Independent devices, especially such as wall suction involve long tubes, as the actual site of the procedure may be at a variable distance from the site of such machine or connection. This long tube may create a tension that tends to pull the suction catheter away from the patient site and to fall to the ground. This tension also makes the procedure inconvenient and error prone. There is accordingly a need to avoid disconnection due to weight, force or entanglement by developing a device that is required to be optimally placed on the ground close to the head end of the patient being resuscitated.

The immediate area surrounding a patient requiring resuscitation constitutes valuable real estate—as it is often crowded with equipment as well as health care personnel. In such circumstances, having an additional device creates challenges for the work-flow. Additionally, long tubes arising out of an independent device, often positioned at a distance from the patient field, may lead to the risk of disconnection (due to weight, tugging force or entanglement) at one or more points—leading to a potentially life threatening failure. There is accordingly a need for a compact space efficient integrated device that can be positioned in the vicinity of a patient.

In healthcare settings, especially those with heavy patient load, there is a high likelihood that an independent suction device may be carried away for use or actually be occupied elsewhere at the time a patient needs resuscitation. For instance in a labor room setting, an independent patient device may be used for providing care to the mother and end up being unavailable for the newborn baby for whom it may be lifesaving. Moreover, shifting a single independent device from the mother's side to the baby's side may waste valuable seconds. An integrated suction and ventilation device is accordingly called for.

While the prior art describes suction machines of various types (central, foot operated and electrical) that provide respiratory gases at high pressures (up to 400 cm $H_2O$), deliberate or inadvertent application of such high pressures to certain patient groups such as newborn babies is known to be harmful by causing mucosal damage and even suppressing respiratory drive via vagal stimulation. There is accordingly a need to for devices that implement in-built protection for sensitive patient groups, by limiting negative pressure that can be generated Prior art devices have additionally comprised suction machines wherein a reservoir for aspirated material is located at a distance from the site of aspiration. The aspirate thus travels along long tube that gets soiled and presents a challenge for cleaning. Long suction tubes that are not cleaned regularly sustain growth of harmful bacteria increasing the overall bacterial load of the care setting and increasing the risk of hospital acquired infections. There is accordingly a need for a device that enables retention of aspirated material in a container close to the point of suction.

The present invention addresses these and other drawbacks in the art.

SUMMARY OF THE INVENTION

The invention relates to an apparatus for manual positive pressure ventilation. The apparatus includes an ergonomic foot pedal comprising a housing, a footplate and a pivot. In an embodiment, the foot pedal is configured for implementing foot operated switching between a first position and second position, the foot pedal comprising (i) a housing configured to accommodate one or more components; (ii) a footplate comprising a first end and a second end; and (iii) a pivot coupling the footplate to the housing, such that the footplate is pivotable about a centre of rotation, between (a) a first position where the first end of the footplate is urged towards the base and the second end of the footplate is urged away from the base; and (b) a second position where the first end of the footplate is urged away from the base and the second end of the footplate is urged towards the base, wherein (a) a ratio of (i) the distance between the centre of rotation and the second end to (ii) the distance between the centre of rotation of said pedal and the first end is between 1:2 and 2:7; and (b) a perpendicular distance between the footplate and a lower surface of the base, along a perpendicular axis passing through the centre of rotation is between 51 mm and 61 mm.

In an embodiment, a maximum angular deviation from a horizontal plane that is capable of being achieved by the footplate in pivoting about the centre of rotation, is less than 14 degrees.

In an another embodiment, the foot pedal is configured such that force of above 100 Newton is required to move the footplate between one of the first position and the second position, and the other of the first position and the second position.

In a particular embodiment, the one or more components of the foot pedal include at least one compressible fluid reservoir disposed between the base and the footplate, such that movement of the footplate between one of the first and second positions and the other of said first and second positions, compresses the at least one compressible fluid reservoir.

In a specific embodiment, the invention comprises a height adjustable stopper positioned within the housing and configured such that the selected height of the stopper defines at least one of the first position and the second position.

The invention further includes a resuscitation pedal comprising (i) a housing, (ii) a footplate, (iii) a pivot, (iv) a set of ventilation reservoirs, and (v) a set of suction reservoirs. In an embodiment, the resuscitation pedal comprises (a) housing configured to accommodate a plurality of compressible fluid reservoirs, the housing comprising a base; (b) a footplate comprising a first end and a second end; (c) a pivot coupling the footplate to the housing, such that the footplate is pivotable about a centre of rotation, between (i) a first position where the first end of the footplate is urged towards the base and the second end of the footplate is urged away from the base; and (ii) a second position where the first end of the footplate is urged away from the base and the second end of the footplate is urged towards the base; (d) a set of ventilation reservoirs, comprising at least one compressible fluid reservoir disposed between the base and the footplate, wherein the set of ventilation reservoirs includes (i) at least a first fluid inlet that enables fluid to be drawn into the set of ventilation reservoirs; and (ii) at least, a first fluid outlet configured for coupling with an airway interface through a ventilation conduit, wherein the ventilation conduit is configured to provide fluid passageway between the set of ventilation reservoirs and the airway interface; and (e) a set of suction reservoirs, comprising at least one compressible fluid reservoir disposed between the base and the footplate, wherein the set of suction reservoirs includes (i) at least a second fluid inlet configured for coupling with a suction conduit; and (ii) at least a second fluid outlet configured to enable fluid to be expelled from the set of suction reservoirs, wherein the set of ventilation reservoirs and the set of suction reservoirs are positioned such that movement of the footplate between one of the first and second positions and the other of said first and second positions, compresses one or more of the compressible fluid reservoirs, and wherein a fluid space within the set of ventilation reservoirs is isolated from the fluid space within the set of suction reservoirs.

In an embodiment, the footplate includes one or more rockers that are configured to engage with the base, and that enable the footplate to transition from one of the first and second positions to the other of the first and second positions through a rocking motion.

In another embodiment, the one or more rockers comprise one or more L-shaped or arcuate rockers.

In a particular embodiment, the set of ventilation reservoirs comprises a plurality of compressible fluid reservoirs, each in fluid communication with each other and with the first fluid inlet and first fluid outlet.

In an embodiment, one or more fasteners of the resuscitation pedal is configured to fasten a surface of at least one compressible fluid reservoir to an internal surface of the footplate.

In a specific embodiment, the set of ventilation reservoirs and the set of suction reservoirs are all positioned between the centre of rotation of the footplate and the first end of the footplate, or are all positioned between the centre of rotation of the footplate and the second end of the footplate.

In another embodiment, the set of ventilation reservoirs are positioned between the centre of rotation of the footplate and the first end of the footplate, and the set of suction reservoirs are positioned between the centre of rotation of the footplate and the second end of the footplate.

In an embodiment, at least one compressible fluid reservoir within the set of ventilation reservoirs or the set of suction reservoirs includes a resilient member disposed therein, and which resilient member is configured to urge the compressible fluid reservoir from a compressed configuration towards an expanded configuration.

In a specific embodiment, a perpendicular distance between the footplate and a lower surface of the base along a perpendicular axis passing through the centre of rotation is between 51 mm and 61 mm.

In another embodiment, a maximum angular deviation from a horizontal plane that is capable of being achieved by the footplate in pivoting about the centre of rotation, is less than 14 degrees.

In a specific embodiment, a ratio of (i) the distance between the centre of rotation and the second end to (ii) the distance between the centre of rotation of said pedal and the first end is between 1:2 and 2:7.

In an embodiment, the resuscitation pedal is configured such that force of above 100 Newton is required to move the footplate between one of the first position and the second position, and the other of the first position and the second position.

In an another embodiment, the resuscitation pedal comprises a hub disposed within the housing, said hub comprising (i) an interface configured to engage with the ventilation conduit; (ii) an interface configured to engage with the suction conduit; (iii) a plurality of reservoir mounts, wherein each reservoir mount provides an interface for mounting a compressible fluid reservoir such that each compressible fluid reservoir is in fluid communication with one of the ventilation conduit and the suction conduit; and (iv) a plurality of conduit passageways connecting the reservoir mounts and configured such that (a) each compressible fluid reservoir within the set of ventilation reservoirs is in fluid communication with the other compressible fluid reservoirs within the set of ventilation reservoirs, and with the first fluid inlet and the first fluid outlet; (b) each compressible fluid reservoir within the set of suction reservoirs is in fluid communication with the other compressible fluid reservoirs within the set of suction reservoirs, and with the second fluid inlet and the second fluid outlet; and (c) the fluid space within the set of ventilation reservoirs is isolated from the fluid space within the set of suction reservoirs.

In a specific embodiment, the hub is removeably disposed within the housing.

The invention also includes an apparatus comprising a hub for mounting compressible fluid reservoirs within a resuscitation pedal having a housing configured to accommodate a set of compressible ventilation reservoirs and a set of compressible suction reservoirs, said hub comprising (i) an interface configured to engage with one of a ventilation conduit and a suction conduit; (ii) one or more reservoir mounts, wherein each reservoir mount provides an interface for removeably mounting a compressible fluid reservoir such that the mounted compressible fluid reservoir is in fluid communication with one of the ventilation conduit and the suction conduit; and (iii) one or more conduit passageways connecting the interface to one or more mounted compressible fluid reservoirs.

In an embodiment, the hub comprises (i) a first interface configured to engage with a ventilation conduit; (ii) a second interface configured to engage with a suction conduit; (iii) a plurality of reservoir mounts comprising a set of ventilation reservoirs and a set of suction reservoirs; and (iv) a plurality of conduit passageways connecting each of the reservoir mounts with one of the ventilation conduit and suction conduit, wherein the reservoir mounts and conduit passageways are configured such that the fluid space within the set of ventilation reservoirs is isolated from the fluid space within the set of suction reservoirs.

The invention further includes a safety apparatus for controlling pressure of ventilation gas delivered through an airway interface, the safety apparatus comprising (i) a pressure release valve provided on a fluid passageway connecting a ventilation pump and an airway interface, configured to respond to an abnormal pressure event by releasing ventilation gas through one or more release orifices into the atmosphere; and (ii) a fluid passageway constriction disposed in a fluid passageway between the ventilation pump and the pressure release valve, wherein the fluid passageway constriction is configured such that the maximum rate of airflow permitted through said constriction is less than or equal to the maximum rate of airflow permitted through said one or more release orifices.

In an embodiment, the fluid passageway constriction comprises an removeable occluder disposed in the fluid passageway between the ventilation pump and the pressure release valve, wherein the occluder is configured to partially obstruct the fluid passageway such that at its narrowest dimension the maximum rate of airflow permitted through said occluder is less than or equal to the maximum rate of airflow permitted through said one or more release orifices.

The invention further comprises an apparatus including an ergonomic foot pedal configured for implementing foot operated switching between a first position and second position, the foot pedal comprising (i) a base configured to accommodate one or more components; and (ii) a foot support comprising an L-shaped rocker having a first end and a second end, wherein said foot support is pivotable about a centre of rotation between (a) a first position where the first end of the foot support is urged towards the base and the second end of the foot support is urged away from the base; and (b) a second position where the first end of the foot support is urged away from the base and the second end of the foot support is urged towards the base.

In an embodiment, the one or more components of the ergonomic foot pedal include at least one compressible fluid reservoir disposed on the base, such that the at least one compressible fluid reservoir is compressed in response to movement of the foot support between one of the first and second positions and the other of said first and second positions.

In another embodiment, the L-shaped rocker is configured to support a first part of an operator's foot such that, responsive to the foot support moving from one of the first position and the second position to the other of the first position and the second position, a second part of the operator's foot directly or indirectly compresses the at least one compressible fluid reservoir.

The invention further comprises an ergonomic foot pedal configured for implementing foot operated switching between a first position and second position, the foot pedal comprising (i) a housing configured to accommodate one or more components, wherein the housing comprises a cylindrical outer shell; and (ii) one or more hemispherical compressible fluid reservoirs disposed within the housing; and (iii) a foot rest surface, wherein the foot rest surface is movable between (a) a first position wherein the foot rest surface is urged towards a base of the cylindrical outer shell; and (b) a second position wherein the foot rest surface is urged away from the base of the cylindrical outer shell; and wherein movement of the foot rest surface from one of the first position and second position to the other of the first position and second position compresses the one or more hemispherical compressible fluid reservoirs.

The invention additionally comprises an ergonomic foot pedal configured for implementing foot operated switching between a first position and second position, the foot pedal comprising: (i) a housing configured to accommodate at least one compressible fluid reservoir; and (ii) a footplate comprising a first end and a second end; and (iii) a pivot coupling the footplate to the housing, such that the footplate is pivotable about a centre of rotation, between (a) a first position where the first end of the footplate is urged towards the base and the second end of the footplate is urged away from the base; and (b) a second position where the first end of the footplate is urged away from the base and the second end of the footplate is urged towards the base; wherein the foot pedal is configured such that angular movement of the footplate is translated to horizontal movement of a shaft, wherein said shaft is configured such that horizontal movement triggers an expiration stroke of the compressible fluid reservoir.

The invention also comprises an ergonomic foot pedal configured for implementing foot operated switching between a first position and second position, the foot pedal comprising (i) a housing configured to accommodate at least one compressible fluid reservoir; and (ii) a footplate comprising a first end and a second end; (iii) a pivot coupling the footplate to the housing, such that the footplate is pivotable about a centre of rotation, between (a) a first position where the first end of the footplate is urged towards the base and the second end of the footplate is urged away from the base; and (b) a second position where the first end of the footplate is urged away from the base and the second end of the footplate is urged towards the base; and (c) a resilient member positioned between the centre of rotation and one of the first end and the second end of the footplate and configured to urge the footplate away from a base of the housing; wherein the resilient member is configured such that resilient force exerted by the resilient member triggers compression of the compressible fluid reservoir.

The invention also includes a safety apparatus for controlling pressure of ventilation gas delivered through an airway interface, the safety apparatus comprising a fluid passageway resistance disposed in a fluid passageway between the ventilation pump and an airway interface, wherein the fluid passageway resistance is a resistance that causes a pressure drop of 30 to 50 cm of $H_2O$ at a flow rate of 10 litres/minute.

The invention also comprises a positive end expiratory pressure device for a ventilation apparatus, comprising a resilient expansile segment disposed on a fluid passageway between a ventilation pump and an airway interface, wherein the expansile segment is configured such that (i) responsive to a ventilation stroke the expansile segment is forced into an expanded state by air entering the expansile segment under pressure and (ii) responsive to the recovery stroke, the expansile segment contracts, wherein contraction of the expansile segment creates positive pressure on a subject's airway during exhalation.

In an embodiment, the expansile segment of the positive end expiratory pressure device is disposed on the fluid passageway and incorporates (i) a one-way inlet valve and (ii) a high resistance outlet orifice, configured such that the rate of inflow into the expansile segment is higher than the rate of outflow therefrom.

The invention also comprises a ventilation apparatus for expelling ventilation gas from a ventilation gas reservoir at a constant pressure and flow, the apparatus comprising (i) a cylinder comprising a first end and a second end, configured to store ventilation gas and having a ventilation gas outlet;

(ii) a piston disposed within the cylinder in an interference with the internal walls of the cylinder, wherein the piston is moveable between the first end and the second end of the cylinder; and (iii) a mount for mounting a weight on the ventilation apparatus such that the mounted weight urges the piston from the first end towards the second end of the cylinder, wherein said movement of the piston from the first end to the second end of the cylinder expels ventilation gas from the cylinder through the ventilation gas outlet.

BRIEF DESCRIPTION OF THE ACCOMPANYING DRAWINGS

DESCRIPTION OF THE INVENTION

The present invention provides a compact and integrated device that enables a care provider to provide positive pressure ventilation to a subject's airways and lungs, whose spontaneous ventilation is either absent or inadequate to maintain metabolic requirements, and to optionally apply suction for the purpose of aspirating mucous, secretions, meconium, blood, fluids or other such materials from a patient—specifically from airways.

Figure 3:
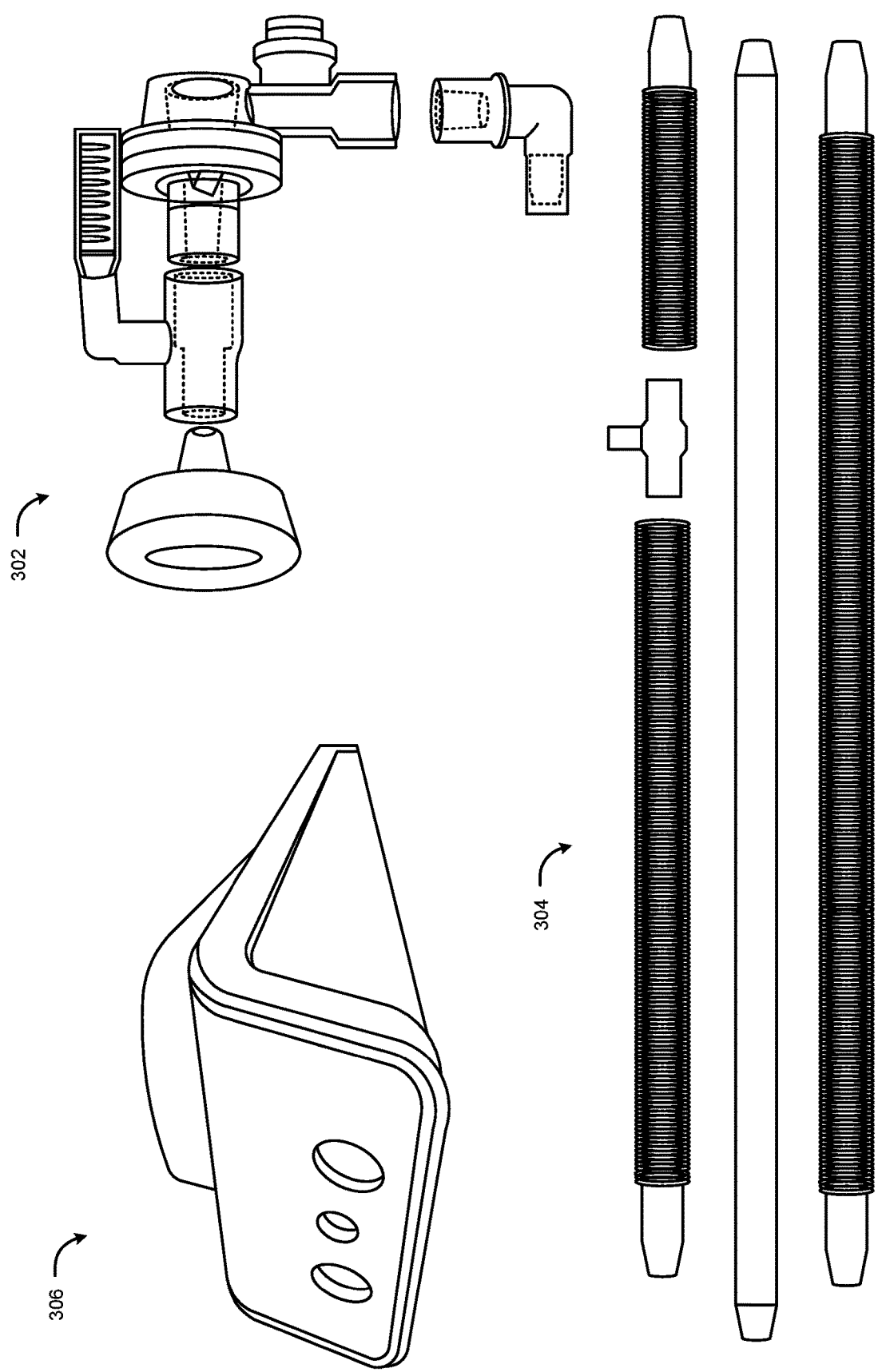
FIG. 3 illustrates components of a resuscitation device in accordance with the present invention.

As illustrated in FIG. 3, the present invention comprises an airway interface 302, a set of conduits or tubes 304 and a pedal 306. Each of these components will be described in further detail hereinbelow.

Figure 4A:
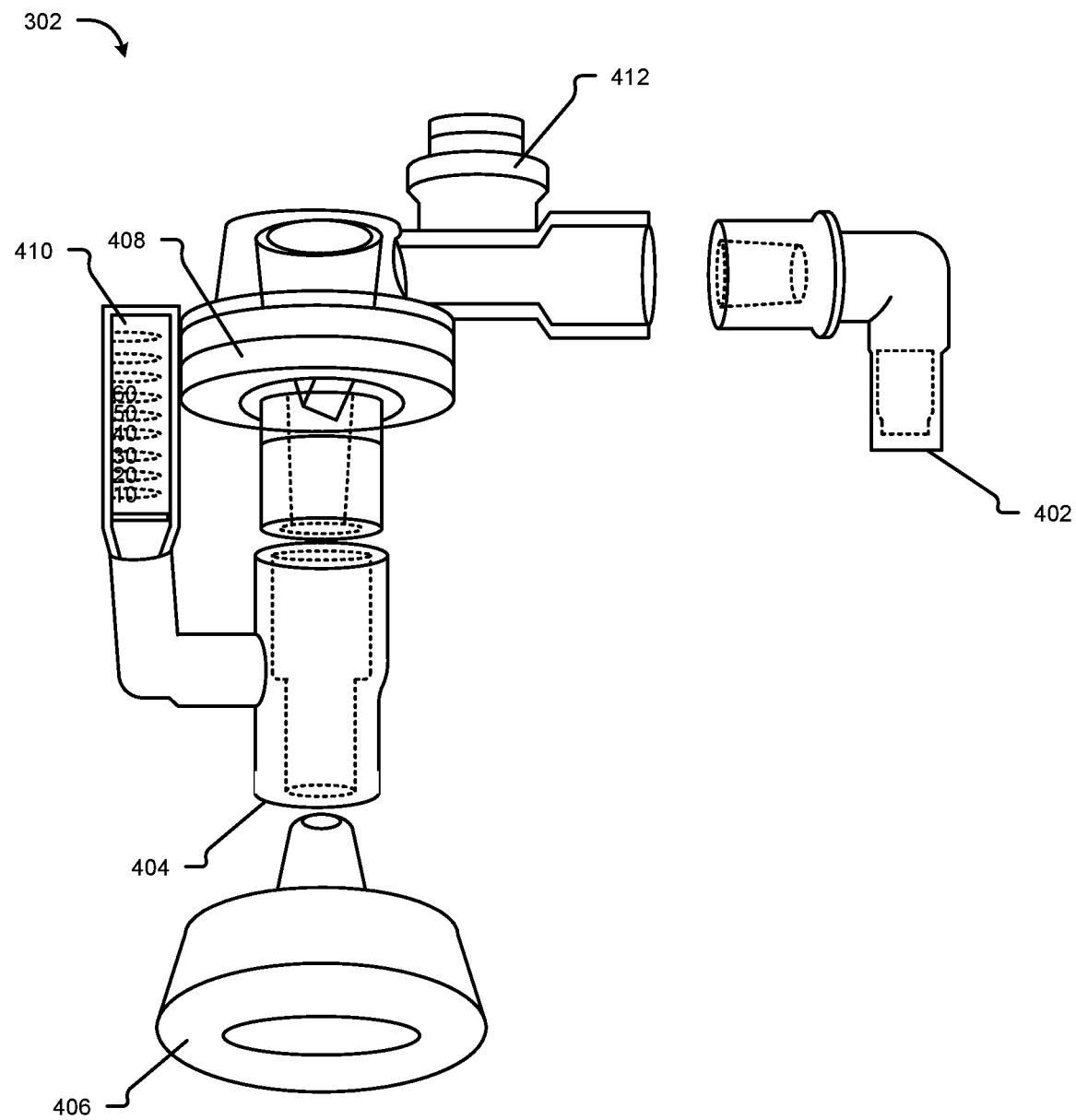
FIG. 4A illustrates an exemplary patient airway interface.
Figure 4B:
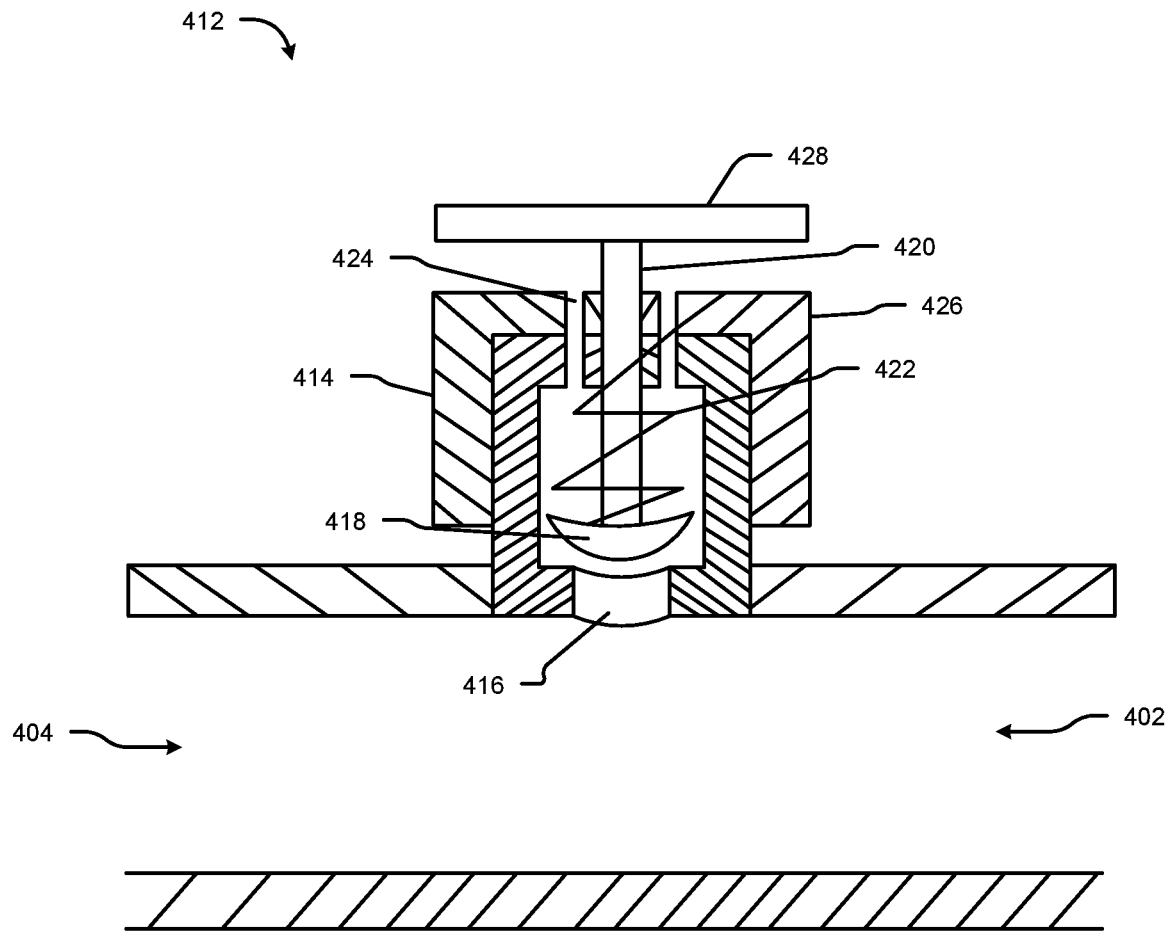
FIG. 4B illustrates an exemplary pressure release valve.

FIGS. 4A and 4B illustrate embodiments of airway interface 302 in accordance with the present invention.

As illustrated in exploded FIG. 4A, airway interface assembly 302 may be connected at an open upstream first end 402 with a gas supply or air supply conduit or tube (not shown). An open downstream second end 404 of airway interface 302 may be connected to a face mask or other airway interface device such as an endotracheal tube, laryngeal mask airway or other suitable interface device 406, wherein open upstream first end 402 and open downstream second end 404 are connected by a fluid path or passage. Gas or air entering airway interface 302 travels from open upstream first end 402 to open downstream second end 404 through said fluid path for delivery to a subject.

Face mask (or other appropriate airway device) 406 provides an interface with a subject's airway and forms a seal about the subject's nose and mouth (in case of mask) or other anatomical counterpart (in case of other airway interface devices). A face mask is typically made of a pliant material and is flexible so as to conform to and provide a sealing fit despite variations in facial anatomy. Face mask 406 could in certain embodiments be replaced by a breathing tube which is inserted down a subject's windpipe.

Airway interface 302 may additionally include a non-rebreather valve arrangement 408 interposed in the fluid path between open upstream first end 402 and open downstream second end 404—for ensuring that air exhaled by a subject is vented to the atmosphere instead of being allowed to travel from open downstream second end 404 back to upstream first end 404. The non-rebreather valve arrangement may be implemented in accordance with one of several different arrangement known in the art, including for example by way of a duck bill valve, which allows gas or air entering open upstream first end 402 to travel to open downstream second end 404, but which redirects exhaled gas or air entering open downstream second end 404 into the atmosphere instead of back to open upstream first end 402. The non-rebreather valve arrangement 408 ensures that a subject receiving ventilation through airway interface 302 only receives fresh gas or air and does not rebreathe exhaled gases.

In an embodiment of the invention, airway interface 302 may include a pressure gauge 410 positioned within the fluid path between open upstream first end 402 and open downstream second end 404, which provides the care provider with information regarding air or gas pressure being delivered to the subject. With access to this information, the care provider can modulate delivery pressure of ventilation gases to ensure that a subject's airways and lungs do not suffer trauma due to ventilation gases accidentally delivered at unacceptably high pressures.

Airway interface 302 may additionally include pressure relief valve 412. As illustrated in FIG. 4B, pressure relief valve 412 may be incorporated into the airway interface 302 between upstream first end 402 and downstream second end 404 to avoid accidental over-pressure conditions. Pressure relief valves have been found to be particularly useful for ventilation devices used for treatment of infants. The pressure release valve 412 has a body 414 and a seat 416. A valve disc 418 is located on rod 420. Spring 422 or any other resilient member may be positioned to urge valve disc 418 into air tight sealing engagement with seat 416—such that under normal or acceptable pressure conditions, the engagement between valve disc 418 and seat 416 prevents air from escaping through pressure relief valve 412. Under overpressure conditions, the air pressure overcomes the force applied by spring 422 and causes valve disc 418 to move out of air tight sealing engagement with seat 416, and permits air to escape out of pressure relief valve 412 through openings 424 in cap 426. Finger button 428 permits an operator to maintain the engagement between valve disc 418 and seat 416 in case it is desired to prevent escape of air through pressure release valve 412 in an overpressure situation.

Figure 5:
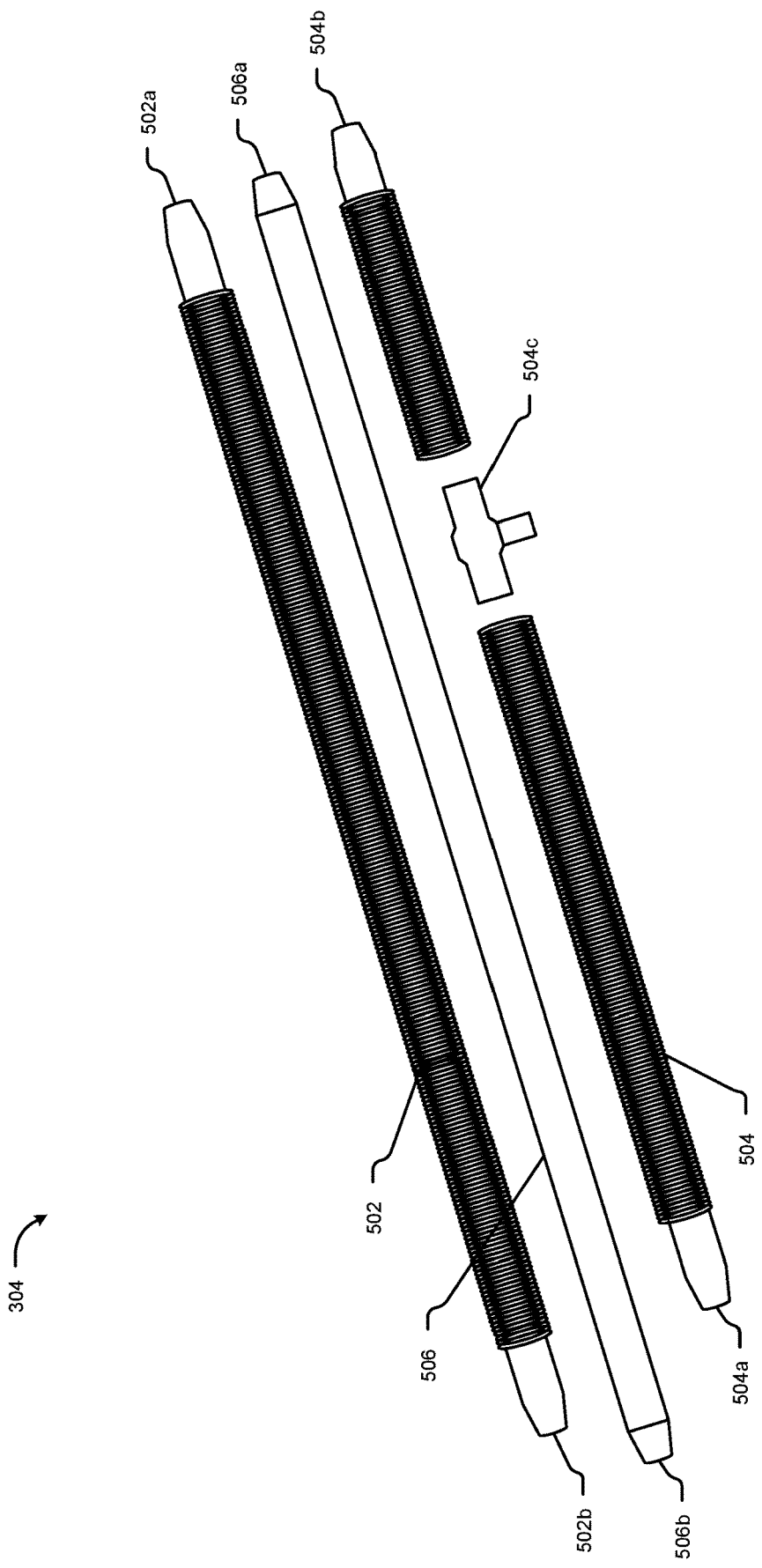
FIG. 5 illustrates an exemplary set of fluid passageway conduits in accordance with the present invention.

FIG. 5 illustrates a set of conduits 304 in accordance with an embodiment of the present invention. The set of conduits 304 illustrated in FIG. 5 comprises a first ventilation conduit 502, a second ventilation conduit 504 and a suction conduit 506. First ventilation conduit 502 comprises an open first end 502a and an open second end 502b having a lumen or fluid path connecting said open first end 502a and said open second end 502b. Second ventilation conduit 504 comprises an open first end 504a and an open second end 504b and has a lumen or fluid path connecting said open first end 504a and open second end 504b. Suction conduit 506 comprises an open first end 506a and an open second end 506b and includes a lumen or fluid path connecting said open first end 506a and said open second end 506b.

In an embodiment of the invention, second ventilation conduit 504 may additionally include a gas inlet port 504c disposed between open first end 504a and open second end 504b.

Open first end 502a of first ventilation conduit 502 may be connected to an outlet of a ventilation pump or compressible ventilation air reservoir, while open second end 502b may be connected to an airway interface of the kind illustrated in FIG. 4A or any other airway interface with or without a pressure release valve and/or a manometer. In an embodiment of the invention, open second end 502b may be connected to open upstream first end 402 of airway interface 302—thereby ensuring that air or other ventilating gas is driven from a ventilation pump through first ventilation conduit 502 to airway interface 302, from where it can be delivered to a subject.

Open second end 504b of second ventilation conduit 504 may be connected to an inlet of the ventilation pump, while open first end 504a may remain open to the atmosphere or may be connected to any selected source of ventilation gas. In an embodiment where the ventilation gas is air drawn from the atmosphere, having first end 504a open to the atmosphere enables the pump to draw fresh air in through open first end 504a of second ventilation conduit 504, which fresh air can thereafter be pumped to the airway interface through first ventilation conduit 502. Either second ventilation conduit 504 or the inlet of the ventilation pump may include a one-way valve to ensure one-way air flow through second ventilation conduit 504 and into the ventilation pump.

Gas inlet port 504c disposed between open first end 504a and open second end 504b of second ventilation conduit 504 enables a desired ventilation or anaesthetic gas (such as for example oxygen or oxygen enriched air) to enter second ventilation conduit 504. The lumen or fluid passageway within second ventilation conduit 504 serves as a fluid reservoir located within the fluid path between the ventilation pump and the airway interface. Accordingly, ventilation gas entering through gas inlet port 504c can accumulate within said second ventilation conduit 504 until a recovery stroke pulls in this air through the inlet tube into a compressible ventilation reservoir, which is then delivered to the patient during the subsequent ventilation stroke. The air delivered to the patient is thus enriched with the supplemental oxygen (or other medical gas) being supplied via port 504C. The dimensions of conduits and reservoir volume is determined in a manner that ensures a reliable relationship between rate of inflow of supplemental gas and the volumetric percentage of such gas in the air gas mixture being delivered to the patient.

This is a novel and useful feature as all methods proposed in prior art to regulate the concentration of supplemental gas in ventilatory-air gas mixture require a continuous supply of air from a pressurized container of air pump under positive pressure, in addition to an additional device known as a blender. The present invention provides the first device of its kind that allows gas concentration regulation in an air-gas mixture without the need for a separate blender and positive pressure supply of air.

In an embodiment of the invention, an inlet to the second end 502a of the air inlet is provided with a component for regulating the diameter of the orifice of this end. A reduced orifice is meant for use when supplemental oxygen supply is being introduced into the air inlet through the oxygen port described previously or through any other point. Such inlet prevents the incoming oxygen from escaping out via the orifice at open end 502a. Instead, the narrow orifice at end 502a leads to a building up of pressure in the air inlet. This pressure transmits into the compressible component and from thereon through the conduits to the patient airway. The orifice is designed so as to ensure that a particular combination of oxygen inflow and orifice diameter leads to a specific amount of pressure being delivered to the patient. This continuous pressure is known as positive end expiratory pressure and is extremely valuable during resuscitation, especially in certain conditions including but not limited to premature newborns.

Open second end 506b of suction conduit 506 may be connected to an inlet of a suction pump (or compressible suction air reservoir) while the open first end 506a may be inserted into a subject's airway (as necessary) to enable application of suction to the subject's airway. Either suction conduit 506 or the inlet of the suction pump may include a one-way valve to ensure one-way air flow through suction conduit 506 and into the suction pump—thereby ensuring that the suction pump does not inadvertently drive unclean air through suction conduit 506 and into a subject's airway.

In another embodiment, the gas inlet port 502c is connected onto air inlet tube 504b, in conjunction with another low pressure release valve.

Figure 1:
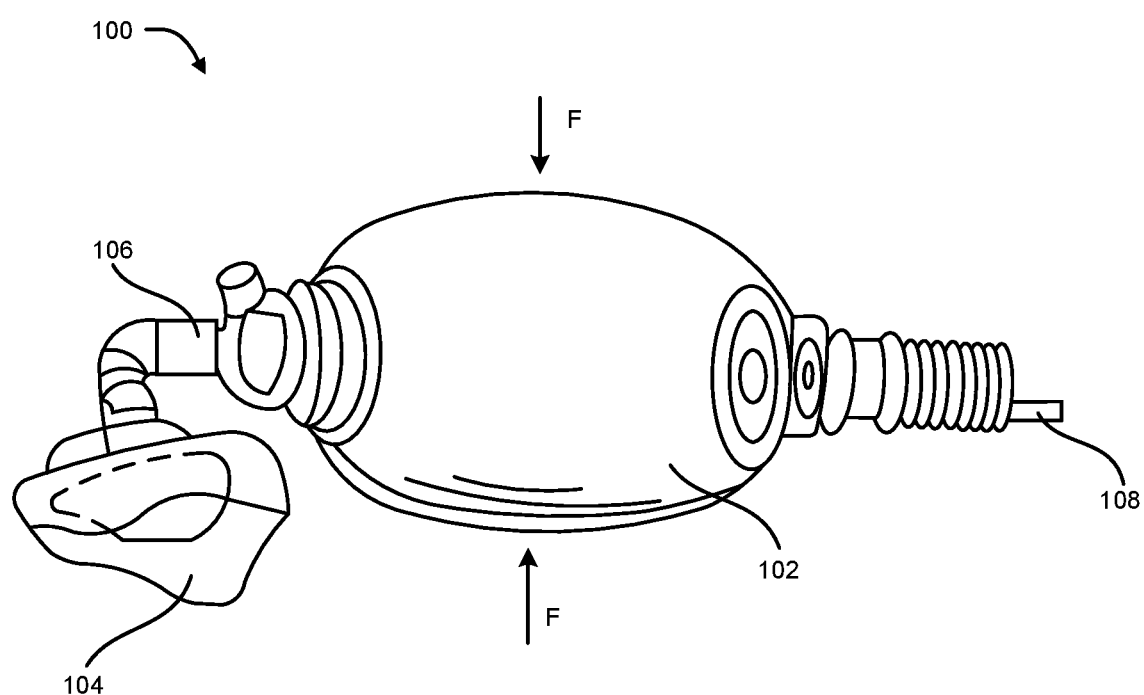
FIG. 1 illustrates a conventional resuscitation device of the bag-mask type.
Figure 2:
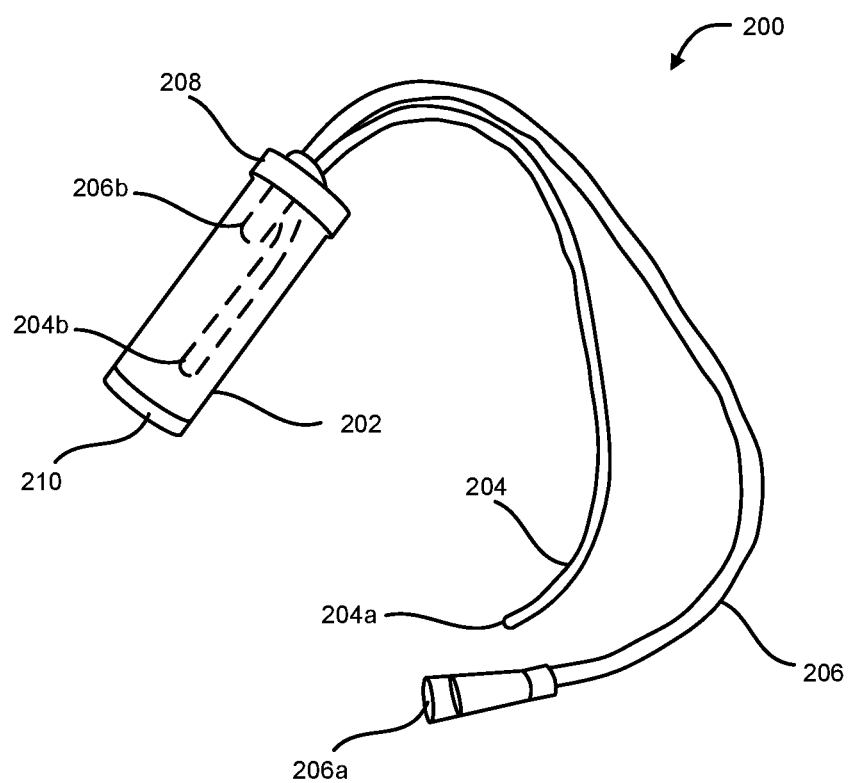
FIG. 2 illustrates a mucous trap.

In an embodiment, a mucous trap (for example mucous trap 202 of the type illustrated in FIG. 2) may be interposed between open first end 506a and open second end 506b of suction conduit 506, such that mucous or other secretions drawn out of a subject's airway and through open first end 506a are captured within the mucous trap and are not allowed to be drawn into the suction pump itself.

In another embodiment, a large liquid reservoir is placed in conjunction with the pedal unit. The inlet of the suction unit is connected to the liquid reservoir, which in turn is connected to the suction tube. A nozzle at the end of the suction tube is connected to suction catheter, which is introduced into a patient's body where suction is sought to be applied.

In an embodiment of the invention any two or more of first ventilation conduit 502, second ventilation conduit 504 and suction conduit 506 may be secured together using a fastener (such as for example a clip, clamp, strap, button fastener, velcro fastener, wire tie, cable tie or ring).

Figure 6A:
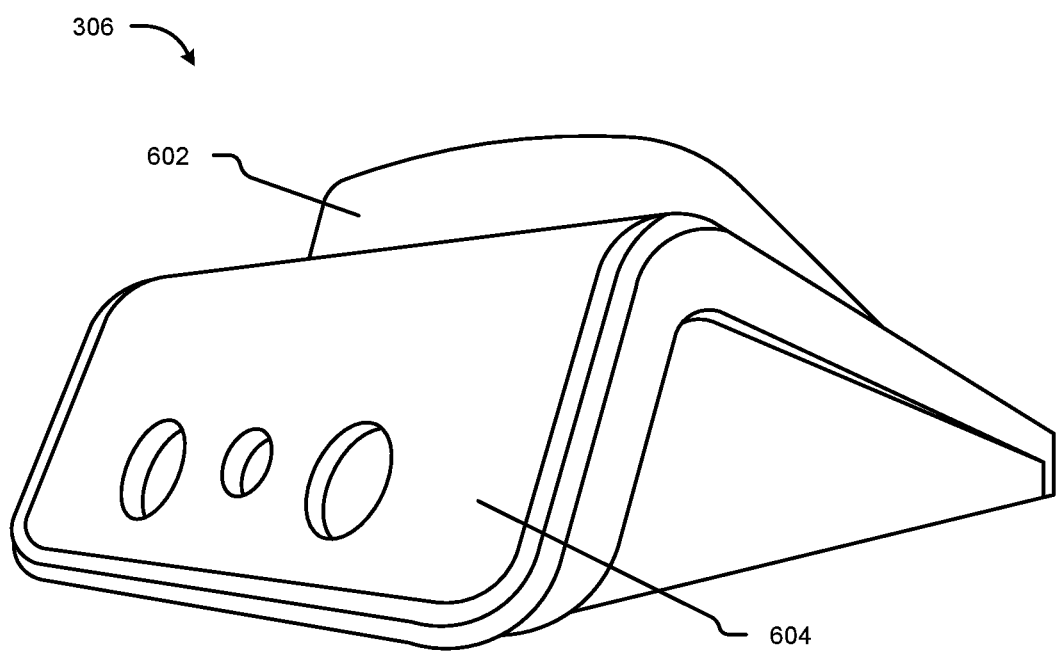
FIGS. 6A to 7 illustrate embodiments of a foot pedal in accordance with the present invention.

FIG. 6A illustrates pedal 306, comprising a footplate 602 and a base 604.

Figure 6B:
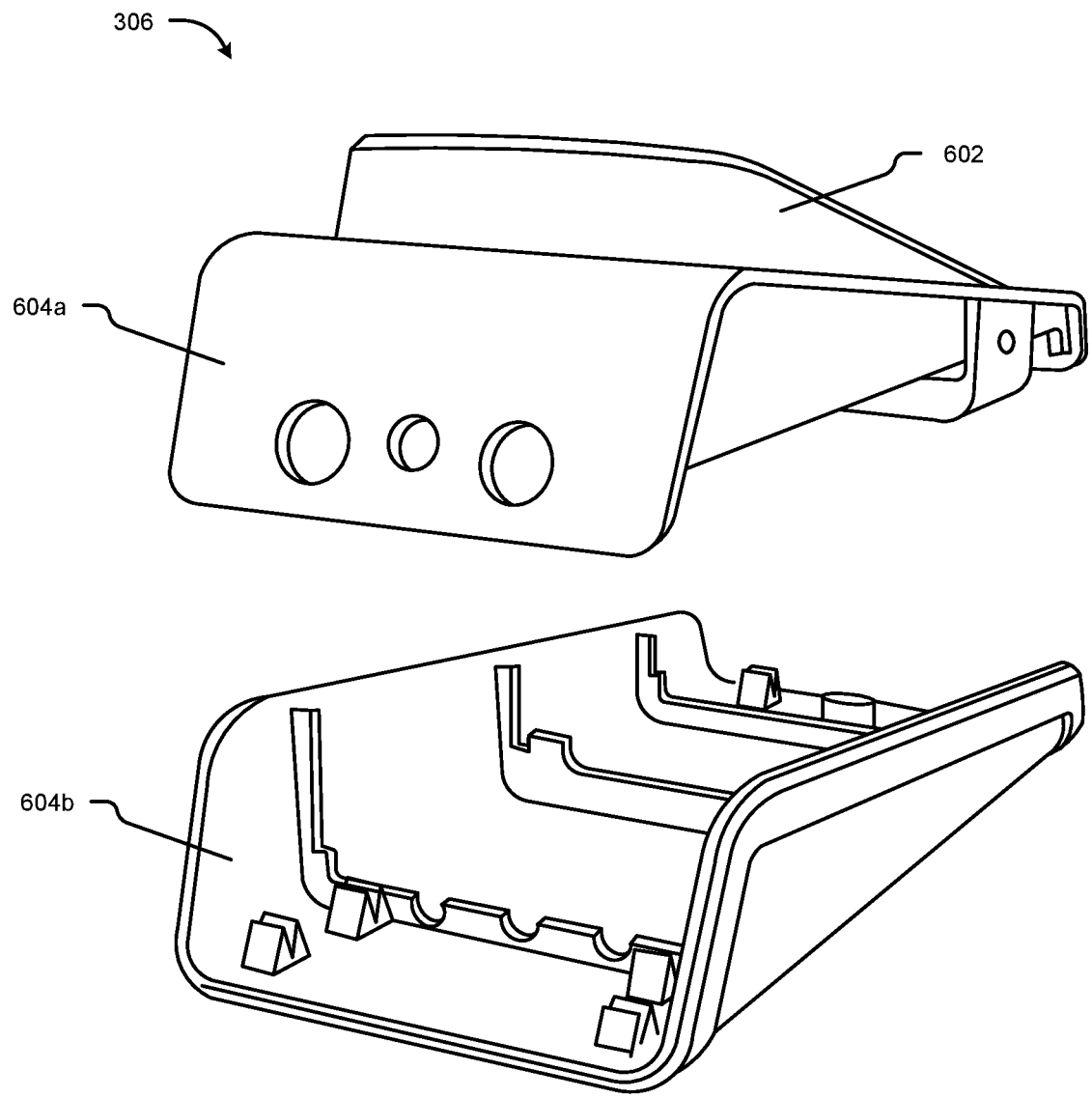

FIG. 6B illustrates an embodiment of the invention, where base 604 comprises an upper base component 604a and a lower base component 604b—which upper and lower base components may be configured to be disengageably coupled to each other, thereby forming a housing capable of accommodating one or more other components of pedal 306.

In another embodiment, upper base and lower base components are fused into a single unit and a u-shaped mounting of the pedal is mounted onto the lower base component in a disengagable fashion. When it is required to access one or more internal components of the pedal, the front part of the pedal is grasped by hand and pulled up. This leads to the rear part of the pedal pressing against the lower base and disengagement of the mounting from the base.

In another embodiment the pedal mounting is fixed non removably to the lower base. Instead the front curved portion of the upper-base (blue part) is made removable. When it is required to access or remove the internal components of the pedal, a stopper underneath the rear vertical wall of the moving pedal part is moved such that it no more obstructs further downward motion of the pedal. The moving pedal part 602 can now be rotated so as to allow a greater angle with the lower base, allowing convenient removal of the internal components.

In another embodiment, the pedal includes a height adjustable stopper such that its height can be precisely adjusted using mechanical or electronic means. Variation in the height of this stopper precisely defines the range of motion of the movable pedal part 602, which in turn precisely sets the volume of air that will be propelled towards or into the patient's lungs on a complete compression of the pedal 602. In this way, the tidal volume delivered can be adjusted. This is especially helpful when the system is used in conjunction with an airway interface device that allows zero or minimal leakage such as an endotracheal tube or others. As such this would be a first foot operated manual resuscitation device that allows volume controlled manual positive pressure ventilation.

In another embodiment, the range of motion of the moving pedal part 602 is restricted using any other modality including but not limited to a stopper at the front part, a stopper under the side walls, a stopper underneath the top plate, a stopper around the axis.

In a further embodiment, one of the compressible air reservoirs may be replaced by a (bottle-cap like) cover, which not only reduces the total volume displaced upon pedal compression (an effect which is also achieved by an adjustable stopper) but also reduces the amount of air displaced per unit angle of compression. This is important while ventilating patients with small tidal volume requirements.

In another embodiment (see FIG. 6D), the resuscitator is designed in a way that a cylindrical outer shell surrounds hemispherical air reservoirs or bellows, which may or may not include a hemispherical movable top cover. The cylindrical outer shell serves as a fulcrum for the point on the operators foot-sole/shoe-sole at the junction between anterior ⅔rds and posterior one third.

In another embodiment, the pedal is designed to contain a metallic cylinder with a piston driven by foot In another embodiment the angular movement of the pedal is converted to a translator horizontal movement of a shaft which either compresses a horizontally aligned bellow or moves a piston inside a horizontally placed cylinder, leading to air being propelled out of such air reservoir and into the patient circuit.

In another embodiment, the compressible air reservoirs are replaced by a hollow spring like metal endoskeleton covered by a thin disposable (stretchable or non stretchable covering). This covering (preferably made of stretchable material is sleeved over an appropriately shaped metal spring endoskeleton, and performs like a bellow. After a single use the outer covering can be disposed and replaced.

Figure 6C:
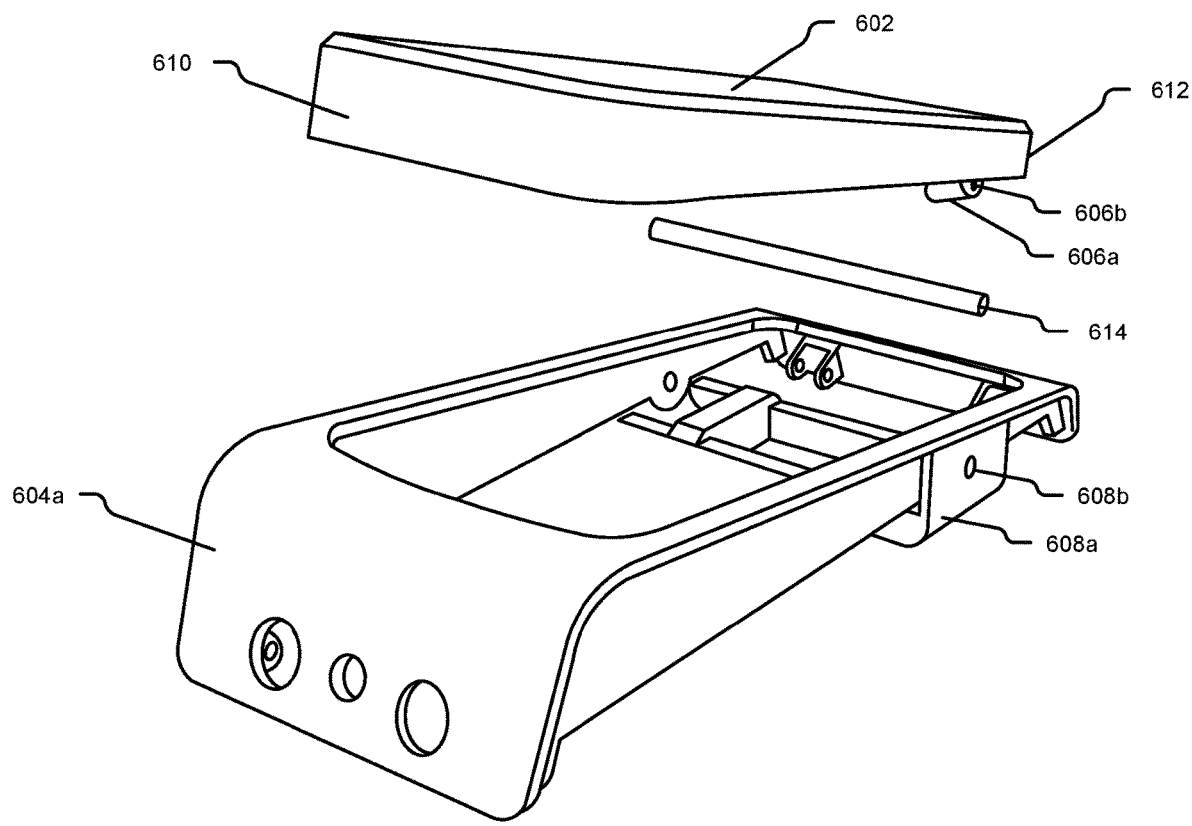
Figure 6D:
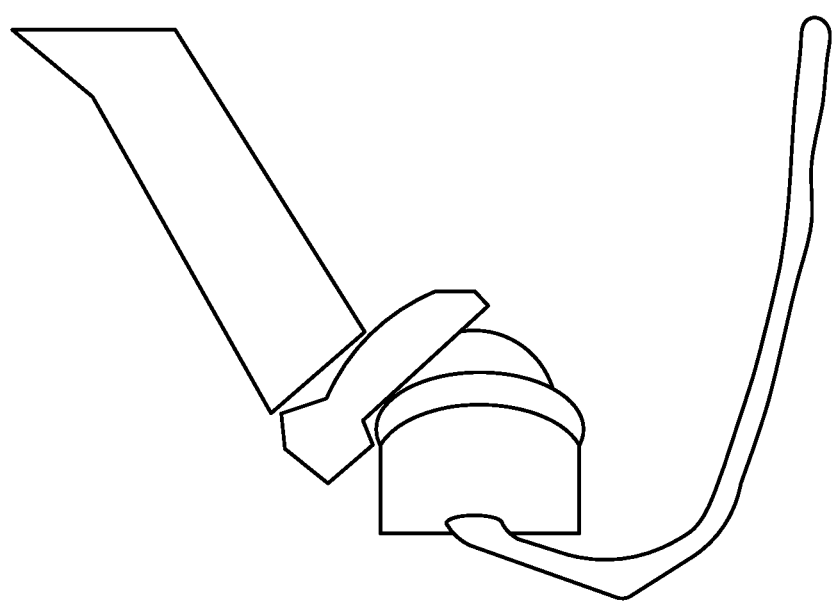

As illustrated in FIG. 6C, footplate 602 has a first end 610 and a second end 612 and may be coupled to base 604 in a manner that permits footplate 602 to move about a fixed centre of rotation, from a first position to a second position in response to a first force, and from a second position back to the first position in response to a second force. For the purposes of the invention, the first position is a position where second end 612 of footplate 602 has been urged towards base 604, while first end 610 of footplate 602 has been urged away from base 604. For the purposes of the invention, the second position is a position where first end 610 of footplate 602 has been urged towards base 604 while second end 612 of footplate 602 has been urged away from base 604.

In the illustrated embodiment, footplate 602 additionally contains one or more pivot mounts 606a having a corresponding channel 606b or recess configured to accommodate pivot shaft 614. Likewise upper base component 604a comprises a pivot mount 608a having a corresponding channel 608b or recess configured to accommodate pivot shaft 614. Pivot shaft 614 may accordingly be used to pivotably mount footplate 602 on base 604 (or upper base component 604a)—which pivoting arrangement ensures that footplate 602 can pivotably move between a first position and a second position. It will be understood that the in the embodiment illustrated in FIG. 6C, pivot shaft 614 acts as the centre of rotation about which footplate 602 pivots between said first position and said second position.

In an embodiment, the ratio of (i) the distance (d1) between a first end of the footplate and the pivot or centre of rotation of said footplate, to (ii) the distance (d2) between the pivot or centre of rotation of said footplate and a second end of the footplate is between 2:1 and 7:2.

Figure 6E:
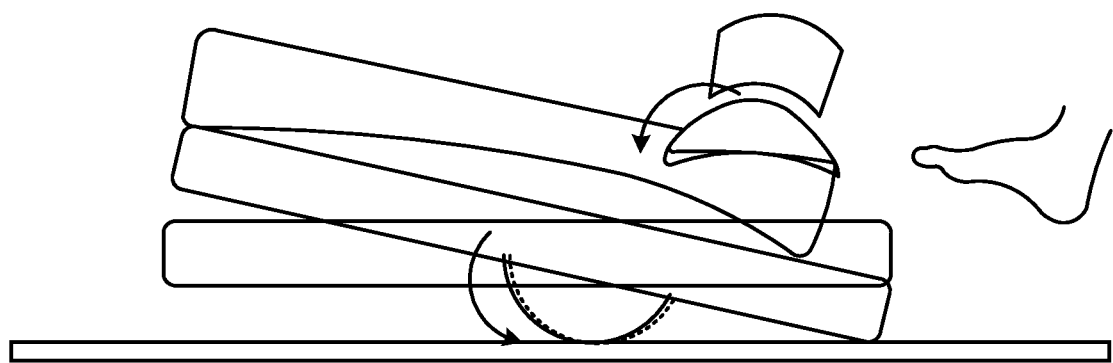
Figure 6F:
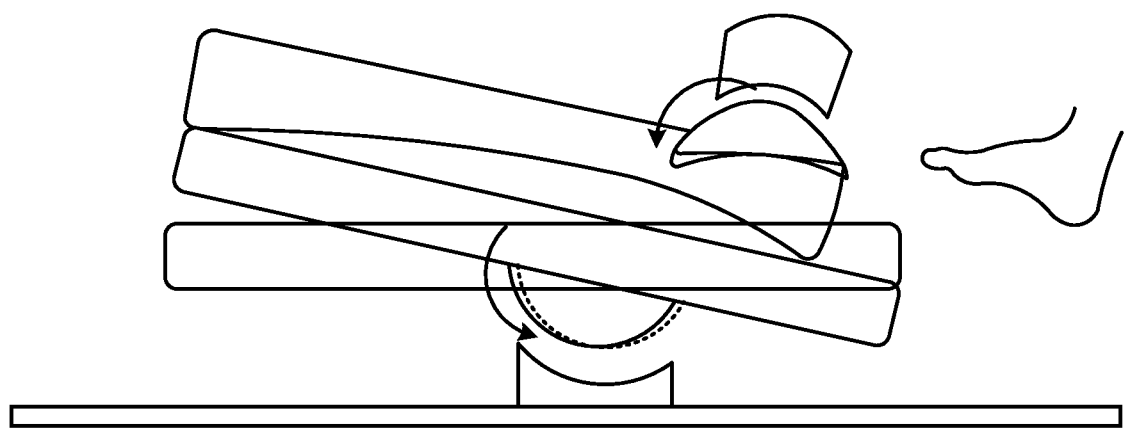

In a different embodiment of the invention (See FIG. 6E and FIG. 6F), the pedal may comprise a small L shaped rocking component (or a component having one or more arcuate members that enable said component to transit through a pivoting or rocking motion about a defined centre of rotation.

Figure 6G:
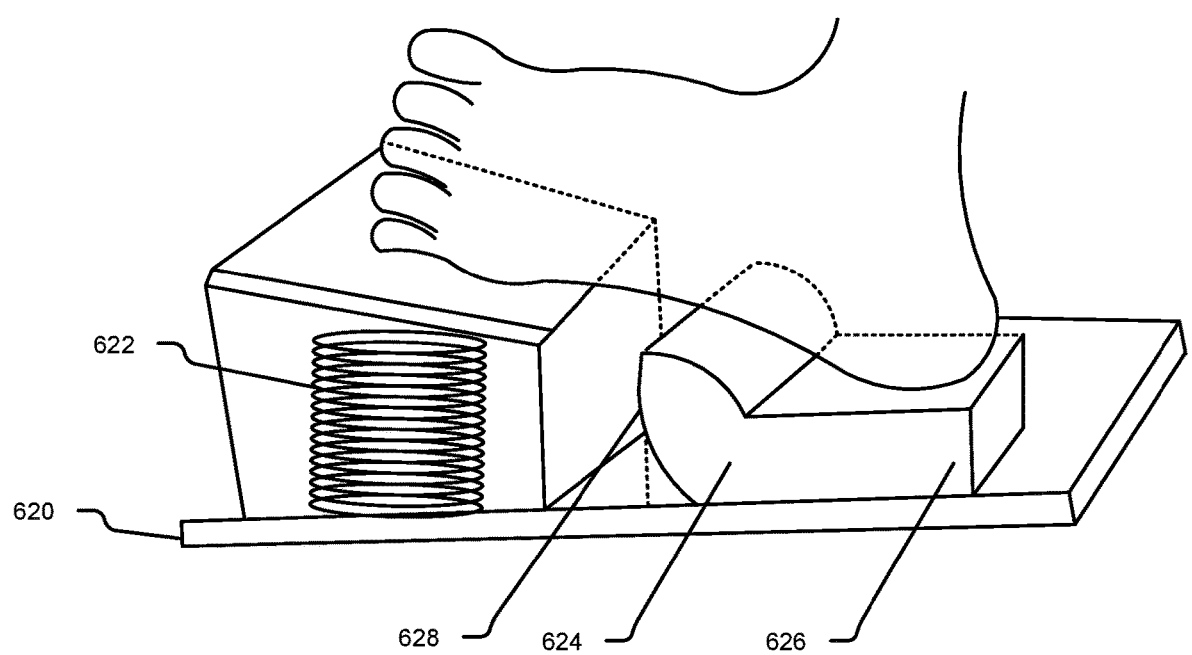

FIG. 6G illustrates a specific embodiment of this invention wherein the pedal comprises a base 620 configured to accommodate one or more components 622, and a foot support 624 comprising an L-shaped rocker having a first end 626 and a second end 628, wherein said foot support is pivotable about a centre of rotation between: (i) a first position where the first end 626 of the foot support 624 is urged towards the base 620 and the second end 628 of the foot support 624 is urged away from the base 620, and (ii) a second position where the first end 626 of the foot support 624 is urged away from the base 620 and the second end 628 of the foot support 624 is urged towards the base 620. The one or more components 622 may include at least one compressible fluid reservoir disposed on the base 620, such that the at least one compressible fluid reservoir is compressed in response to movement of the foot support 624 between one of the first and second positions and the other of said first and second positions.

In the embodiment illustrated in FIG. 6G, the area of the foot sole/shoe sole starting at the junction of the anterior 2 thirds and posterior two-thirds up to the mid-point of the foot-sole/shoe-sole may rest on a second end 628 of foot support 624 while the heel point rests on first end 626. The anterior half of the foot thus projects out. A bellow, compressible reservoir or switch to be compressed lies under the anterior half of the foot/shoe-sole. When the compressible component needs to be compressed, that is done by bringing the anterior half of the foot down. This leads to a "see-saw" like "rocking" motion of the rocking component. Since the system pivots around a virtual moving axis, which itself follows an arcuate path during actuation, the foot encounters least resistance and a smooth motion occurs. This arrangement also helps operators transfer their weight smoothly and effortlessly—partially through the rocking component to the ground (first half of compression time), and partially to the bellow to be compressed (second half of compression time) leading to lesser fatigue, and greater stability and greater comfort. The rocking part is attached to a base plate through suitable means that allow it to move about a virtual axis that moves on an arcuate path, while still ensuring that the latter is firmly attached onto a base plate.

In another embodiment, the L shaped pedal is replaced with a Z shaped structure where a flat horizontal member projecting out at right angle to the vertical L shaped member of the rocking component, this flat, nearly horizontal member serves as a depressor for any reservoir or switch that may be housed underneath it. When depressed using the foot or any other body part, the air reservoir or switch or other mechanically active part can be compressed in an ergonomic and fatigue free manner.

Alternatively, an arcuate member may extend down from a flat pedal and act as a fulcrum for rocking motion of the pedal The arcuate surface of the rocking component is modelled on (similar in shape to) the articular surface of the human tibia bone within the ankle joint.

In another embodiment, the articulation region of the rocking component is designed in a manner to replicate the ankle joint, thus creating a force parallelogram between the ankle joint and the rocking component.

Figure 7:
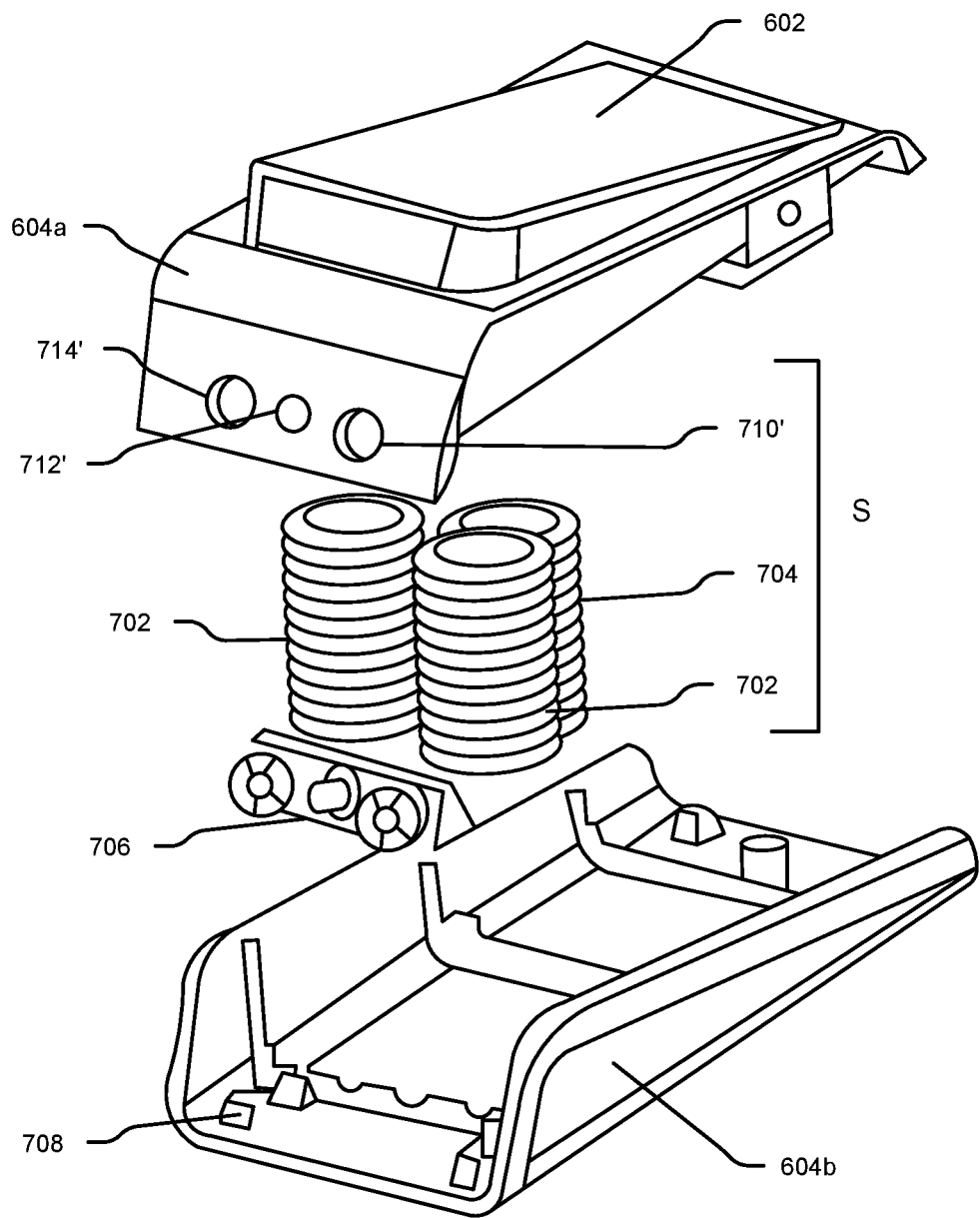

FIG. 7 illustrates an exploded view of pedal 306, including additional components of the resuscitation and suction device in accordance with the present invention. As shown in FIG. 7, footplate 602 and base 604 (comprising upper base component 604a and lower base component 604b) define an interior space, which interior space S may house pump or drive mechanisms for ventilation and suction purposes.

In the embodiment illustrated in FIG. 7, the interior space S houses a ventilation pump or drive mechanism comprising one or more compressible air reservoirs or compressible air-spaces or compressible ventilation bellow(s) 702 and 702'. Interior space S also houses at least one compressible air reservoir such as a bellow which can act as a suction component 704. In an embodiment where interior space S houses one or more interconnected ventilation bellows 702 and 702', said ventilation bellows may be in fluid communication with each other (for example, by way of one or more fluid paths interconnecting said plurality of ventilation bellows. The suction bellow 704 is at all times maintained in hermetic isolation from ventilation bellows 702 and 704.

Interior space S additionally houses pedal hub 706, which is described in further detail in connection with accompanying FIG. 8. As illustrated in FIG. 7, the pedal may include one or more fasteners 708 which fasteners (either independently or in cooperation with corresponding fasteners on pedal hub 706) can be used to disengageably or permanently affix pedal hub 706 at a desired location within pedal 306. Said fasteners may include clasps, buttons, screws, rivets, recesses, protrusions, snap fit flanges or combinations thereof.

Figure 8:
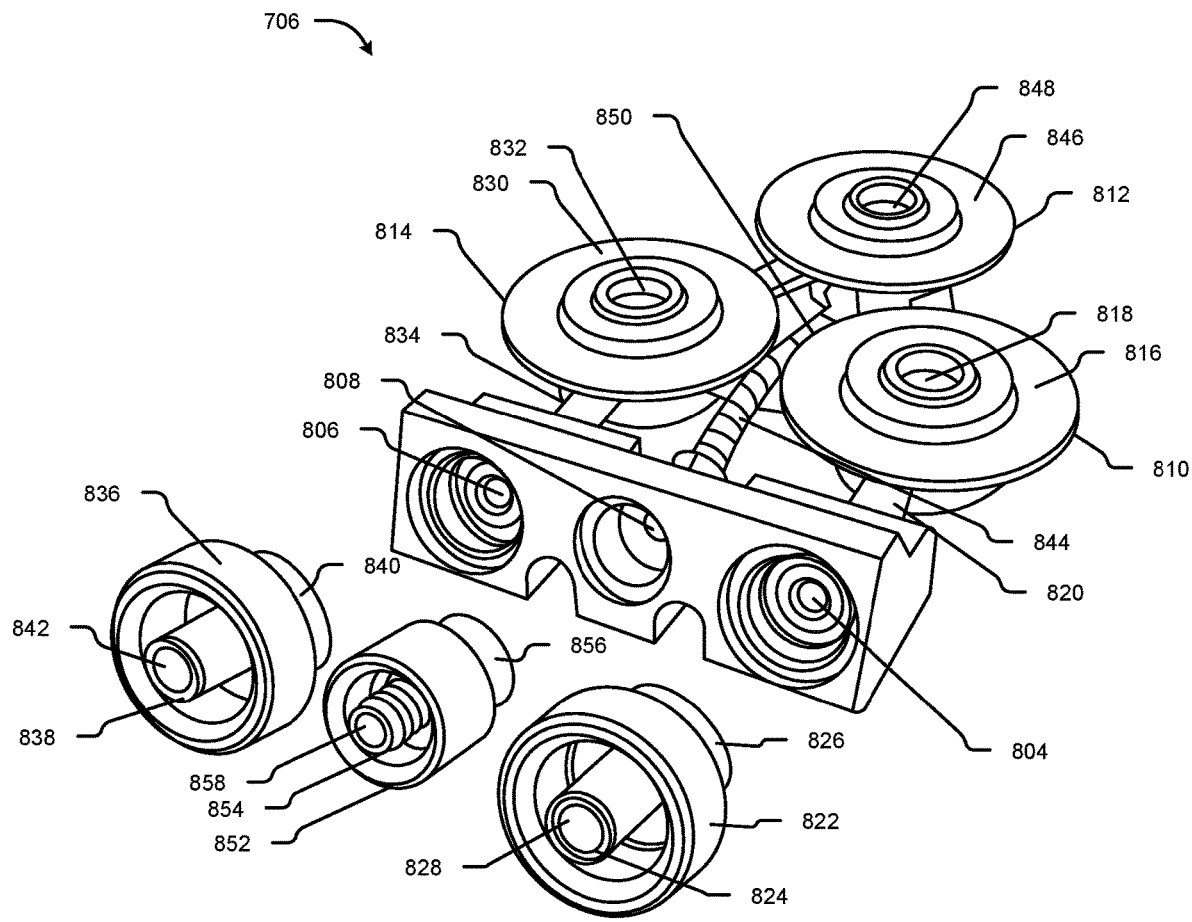
FIG. 8 illustrates a resuscitation hub in accordance with the present invention.

As illustrated in FIG. 8, hub 706 includes hub body 802, ventilation outlet 804, ventilation inlet 806 and suction inlet 808. Hub 706 additionally includes a plurality of bellow mounts 810, 812 and 814, each configured to mount a corresponding compressible ventilation or suction reservoir thereon.

As illustrated in FIG. 8, compressible reservoir mount 810 comprises compressible reservoir mount disk 816, said compressible reservoir mount disk having compressible reservoir mount disk orifice 818 provided therein. Compressible reservoir mount disk orifice 818 is interconnected with ventilation outlet 804 by means of interconnection member 820. Interconnection member 820 may comprise a rigid or flexible pipe or lumen interconnecting and providing a fluid path between ventilation outlet 804 and compressible reservoir mount disk orifice 818—such that gas, air or fluid driven through one of ventilation outlet 804 and compressible reservoir mount disk orifice 818 travels through interconnection member 820 and out of the other of ventilation outlet 804 and compressible reservoir mount disk orifice 818.

In an embodiment, the invention may include a cup like structure onto which the compressible reservoir mount disk is mounted. From this cup like structure, the interconnection members 820 and 844 originate. Also in the current embodiment the compressible reservoir mount discs may be mounted onto the cup type structure with the help of threads and O rings.

Compressible reservoir mount disk 816 may be configured to permit a corresponding compressible ventilation reservoir to be mounted thereon in fluid tight engagement, such that air driven out of the mounted compressible ventilation reservoir in response to compression of the reservoir, travels through compressible reservoir mount disk orifice 818, interconnection member 820 and out of ventilation outlet 804.

FIG. 8 additionally illustrates ventilation outlet connection member 822 having first end 824, second end 826 and a lumen (or other fluid path) 828 connecting said first end 824 and said second end 826. Second end 826 may be configured for disengageable fluid tight engagement with ventilation outlet 804 (for example by way of screw threads, a snap-fit arrangement, or an interference fit, and optionally including one or more o-rings), while first end 826 may be configured for disengageable fluid tight engagement (for example, by way of screw threads, a snap-fit arrangement, or an interference fit, and optionally including one or more o-rings) with first end 502a of first ventilation conduit 502 (illustrated in FIG. 5). When connected to first ventilation conduit 502 at one end, and with ventilation outlet 804 at the other end, ventilation outlet connection member 822 establishes a fluid path between second open end 502b of first ventilation conduit 502 and a compressible ventilation reservoir mounted on compressible reservoir mount 810, such that responsive to compression of the mounted compressible reservoir, air or gas is driven from the mounted compressible reservoir through the established fluid path and out of open second end 502b of first ventilation conduit 502. When open second end 502b of first compressible ventilation conduit 502 is connected to an airway interface, which enables gas or air driven from the compressible reservoir mounted on compressible reservoir disk 810 to a patient's lungs.

In an optional embodiment of the invention, the fluid path between the connected airway interface and the reservoir mounted on compressible reservoir disk 810 may include a one-way valve that permits air or gas to be driven from the mounted compressible reservoir and out of the airway interface, but does not permit air or gas exhaled by the subject to return to the mounted compressible reservoir.

FIG. 8 additionally illustrates compressible reservoir mount 814—which comprises compressible reservoir mount disk 830, said bellow compressible reservoir mount disk 830 having compressible reservoir mount disk orifice 832 provided therein.

A compressible reservoir is mounted on compressible reservoir mount 814. Optionally, the compressible reservoir mount disk may be replaced with a bottle cap type of component that simply occludes the top orifice of the compressible reservoir mount container, converting the compressible reservoir mount into a mere conduit. The resultant system with a single compressible reservoir now becomes a resuscitator with a reduced (half) reservoir volume. Along with reducing the maximum deliverable volume delivered upon every complete compression of the pedal, this also reduces the volume propelled per unit compression of the pedal plate, making it easier to regulate volume delivery manually.

Compressible reservoir mount disk orifice 832 is interconnected with ventilation inlet 806 by means of interconnection member 834. Interconnection member 834 may comprise a rigid or flexible pipe or lumen interconnecting and providing a fluid path between ventilation inlet 806 and compressible reservoir mount disk orifice 832—such that when gas, air or fluid driven through one of ventilation inlet 806 and compressible reservoir mount disk orifice 832 travels through interconnection member 834 and out of the other of ventilation inlet 806 and bellow mount disk orifice 832.

Compressible reservoir mount disk 830 may be configured to permit a corresponding compressible ventilation reservoir to be mounted thereon in fluid tight engagement, such air or gas that drawn into the mounted compressible ventilation reservoir in response to expansion of the reservoir, travels through ventilation inlet 806, interconnection member 834 and out of compressible reservoir mount disk orifice 832 into the mounted compressible ventilation reservoir.

FIG. 8 additionally illustrates ventilation inlet connection member 836 having first end 838, second end 840 and a lumen (or other fluid path) 842 connecting said first end 838 and said second end 840. Second end 840 may be configured for disengageable fluid tight engagement with ventilation inlet 806 (for example by way of screw threads, a snap-fit arrangement, or an interference fit, and optionally including one or more o-rings), while first end 838 may be configured for disengageable fluid tight engagement (for example by way of screw threads, a snap-fit arrangement, or an interference fit, and optionally including one or more o-rings) with open second end 504*b* of second ventilation conduit 504 (illustrated in FIG. 5). When connected to second ventilation conduit 504 at one end, and to ventilation outlet 806 at the other end, ventilation outlet connection member 836 establishes a fluid path between first open end 504*a* of second ventilation conduit 504 and a compressible ventilation reservoir mounted on compressible reservoir mount 814. This ventilator inlet connection member 836 contains a one way valve arrangement such that when the compressible reservoir mounted on compressible reservoir mounting disc 814 is compressed, air/gas mixture is unable to escape out of the ventilation inlet connection member into the ventilation inlet conduit. Instead, responsive to expansion of the mounted bellow, air or gas is drawn into the mounted compressible reservoir through open first end 504*a* of second ventilation conduit 504 onward through the established fluid path and into the compressible ventilation reservoir mounted on compressible reservoir mount 814.

It will be immediately observed that this fluid path used for drawing air or gas into the compressible ventilation reservoir and for driving air or gas from a compressible ventilation reservoir into a subject's lungs is entirely separate from, and in hermetic isolation form the fluid path established for the purpose of suction—thereby ensuring that under no circumstances air sucked in from one subject is delivered to back to the same or any other subject. Moreover the airway interface contains a duckbill valve which ensures that no air exhaled by the subject re-enters the conduits. Instead all exhaled air is diverted out from the system by duck bill valve.

In an embodiment of the invention, the fluid path between the open first end 504*a* of second ventilation conduit 504 and the compressible reservoir mounted on compressible reservoir disk 814 may include a one-way valve that permits air or gas to be drawn into from the mounted compressible reservoir, but does not permit air or gas to be driven back out of open first end 504*a* of second ventilation conduit 504.

In an embodiment of the invention compressible reservoir mount 810 and compressible reservoir mount 814 may be interconnected by a rigid or flexible pipe or lumen 844, which interconnects and provides a fluid passageway between compressible reservoir mount disk orifice 818 and compressible reservoir mount disk orifice 832. This arrangement ensures that two separate compressible reservoir may be respectively mounted on bellow mount 810 and bellow mount 814, while enabling the two separately mounted bellows to act as a single reservoir for ventilation gases or air.

In another embodiment a single removable and compressible reservoir may be used instead of two compressible reservoirs for ventilation, which reservoir(s) may be spherical, hemispherical, cuboidal, polygonal or of any other shape.

FIG. 8 additionally illustrates compressible reservoir mount 812—which comprises compressible reservoir mount disk 846, said compressible reservoir mount disk 846 having compressible reservoir mount disk orifice 848 provided therein. Compressible reservoir mount disk orifice 848 is interconnected with suction inlet 808 by means of interconnection member 850. Interconnection member 850 may comprise a rigid or flexible pipe or lumen interconnecting and providing a fluid path between suction inlet 808 and compressible reservoir mount disk orifice 848. The compressible reservoir mount 812 has 2 orifices, first being in front and onto which the interconnecting member connects. This orifice is fitted with a one way valve to ensure that when the corresponding bellow is compressed, it does not allow any air to escape into the interconnecting member and thence into the suction tube. Correspondingly when the compressible reservoir mounted on compressible reservoir mounting disc 846 expands, a negative pressure is generated. At this time the valve opens and transmits the negative pressure through the interconnecting member and thence into the suction tube.

The rear orifice of the compressible reservoir mount 812 has a one way valve oriented such that when the compressible reservoir mounted on mount 812 is compressed all air is released outside the compressible reservoir mount. When the compressible reservoir begins to expand, this valve shuts down and does not allow any air to enter from this orifice, and the entire negative pressure is directed through suction tube.

FIG. 8 additionally illustrates suction inlet connection member 852 having first end 854, second end 856 and a lumen (or other fluid path) 858 connecting said first end 854 and said second end 856. Second end 856 may be configured for disengageable fluid tight engagement with suction inlet 808 (for example by way of screw threads, a snap-fit arrangement, or an interference fit, and optionally including one or more o-rings), while first end 854 may be configured for disengageable fluid tight engagement (for example by way of screw threads, a snap-fit arrangement, or an interference fit, and optionally including one or more o-rings) with open second end 506*b* of suction conduit 506 (illustrated in FIG. 5). When connected to suction conduit 506 at one end, and with suction inlet 808 at the other end, suction inlet connection member 852 establishes a fluid path between open first end 506*a* of suction conduit 506 and a compressible suction reservoir mounted on compressible reservoir mount 812, such that responsive to expansion of the mounted bellow, air or gas is drawn into the mounted compressible reservoir through open first end 506*a* of suction conduit 506, onward through the established fluid path and into the compressible suction reservoir mounted on compressible reservoir mount 812.

It will be immediately observed that this fluid path used for drawing air or gas into the compressible suction reservoir is entirely separate from, and in hermetic isolation from the fluid path established for driving air or gas from a compressible ventilation reservoir into a subject's lungs, and also from the fluid path established for drawing air into the compressible ventilation reservoir—thereby ensuring that mucous, secretion or microbes drawn out during suction from a subject's airways, do not mix with air or gas provided to the subject during ventilation.

In an embodiment of the invention, the fluid path between the open first end 504a of second ventilation conduit 504 and the compressible reservoir mounted on compressible reservoir disk 814 may include a one-way valve that permits air or gas to be drawn into the compressible reservoir, but does not permit air or gas to be driven back out of open first end 506a of suction conduit 506.

In an embodiment of the invention, compressible reservoir mount 812 may include an additional compressible suction reservoir outlet orifice (not shown) positioned to enable air to be driven out of a compressible suction reservoir mounted on compressible reservoir mount 812 in response to compression of said compressible reservoir. Said additional orifice or inlet may include a one way valve positioned to allow air to be driven out of the compressible reservoir from said orifice during compression, but which prevents air from being drawn into said orifice or inlet in response to expansion of the compressible reservoir—thereby ensuring that suction only occurs through suction conduit 506.

Pedal hub 706 may additionally include one or more fasteners (not shown) that (either independently or in cooperation with corresponding fasteners within pedal 306) permit said pedal hub 706 to be removably or permanently affixed at a desired location within pedal 306. Said fasteners may include clasps, buttons, screws, rivets, recesses, protrusions, snap fit flanges or combinations thereof.

It would be understood that the shape and configuration of pedal hub 706 may be selected to ensure that the compressible ventilation reservoir(s) and compressible suction reservoir mounted thereon may be positioned appropriately within pedal 306.

In an embodiment of the invention more generally illustrated in FIGS. 6A to 6C, all of the compressible ventilation reservoirs and the compressible suction reservoirs are positioned between (i) a centre of rotation about which footplate 602 is configured to pivot between its first position and its second position and (ii) first end 610 of footplate 602. In this embodiment, when footplate 602 moves from its second position to its first position, first end 610 of footplate 602 is urged in the direction of base 604, causing the compressible ventilation reservoir(s) and suction bellow positioned between the centre of rotation and first end 610 of footplate 602 to be moved from an expanded state to a compressed state. This compression drives air or ventilation gas from the compressible ventilation reservoir(s) through first ventilation conduit 502, into and through the airway interface. Simultaneously, this movement of footplate 602 causes the compressible suction reservoir to move from an expanded state to a compressed state by driving air out of the corresponding compressible suction reservoir outlet orifice—thereby preparing the compressible suction reservoir for the suction stroke.

During the return stroke, footplate 602 moves from its first position to its second position, thereby allowing the compressible ventilation reservoir(s) and compressible suction reservoir to move from the compressed state to an expanded state—which expansion is accompanied by drawing of air or gas into the respective compressible reservoirs through the various inlets and fluid paths described in detail above. As discussed previously, expansion of the compressible suction reservoir generates suction through suction conduit 506, which suction can be used to clear a subject's airway of mucous, accumulated secretions or other obstructions.

In the above embodiment, movement of the footplate from the second position to the first position triggers the ventilation stroke of the pedal, whereas movement of the footplate from the first position to the second position triggers the suction stroke of the pedal.

In another embodiment of the invention, the compressible ventilation reservoir(s) may be positioned between (i) the centre of rotation of footplate 602 and (ii) one of first end 610 and second end 612 of footplate 602, while the compressible suction reservoir may be positioned between (iii) the centre of rotation of footplate 602 and (iv) the other of first end 610 and second end 612 of footplate 602. In this embodiment, as footplate 602 moves from its second position to its first position, first end 610 of footplate 602 is urged in the direction of base 604, causing compression of the compressible reservoir(s) positioned between the centre of rotation and first end 610. Simultaneously, second end 612 of footplate 602 is urged away from base 604, enabling expansion of the compressible reservoir(s) positioned between the centre of rotation and second end 612.

In an embodiment where the compressible ventilation reservoir(s) are positioned between the centre of rotation and first end 610 and the compressible suction reservoir is positioned between the centre of rotation and second end 612, movement of footplate 602 from the second position to the first position causes first end 610 of footplate 602 to move towards base 604—which compresses the compressible ventilation reservoir(s), and triggers a ventilation stroke of the apparatus by driving air or ventilation gas from the compressible ventilation reservoir(s) through first ventilation conduit 502, and onward through the airway interface. Movement of footplate 602 from the second position to the first position simultaneously causes second end 612 of footplate 602 to move away from base 604—which enables the compressible suction reservoir to expand, thereby triggering a suction stroke of the apparatus by drawing air through suction conduit 506 into the compressible suction reservoir.

Movement of footplate 602 in a return stroke back from the first position to the second position, allows the compressible ventilation reservoir(s) to expand while simultaneously compressing the suction bellow, thereby preparing the pedal for the next ventilation and suction strokes.

In another embodiment of the invention, the compressible suction reservoir may be positioned between (i) the centre of rotation of footplate 602 and (ii) one of first end 610 and second end 612 of footplate 602, while the compressible ventilation reservoir(s) may be positioned between (iii) the centre of rotation of footplate 602 and (iv) the other of first end 610 and second end 612 of footplate 602.

In yet another embodiment of the invention, all of the compressible ventilation reservoirs and compressible suction reservoirs may be positioned between a centre of rotation about which footplate 602 is configured to pivot, and second end 612. In this embodiment, when footplate 602 moves from its first position to its second position (i.e. the second end 612 of footplate 602 is urged in the direction of base 604), the compressible ventilation reservoir(s) and compressible suction reservoir move from an expanded state to a compressed state. This compression of the compressible ventilation reservoir(s) drives air or ventilation gas from the compressible ventilation reservoir(s) through first ventilation conduit 502, and through the airway interface, while simultaneously driving air out of the compressible suction reservoir through a compressible suction reservoir outlet orifice (thereby preparing the compressible suction reservoir for the suction stroke). During the return stroke, footplate 602 moves from its second position to its first position, thereby allowing the compressible ventilation reservoir(s) and compressible suction reservoir to expand from their respective compressed states to expanded states—which expansion is accompanied by drawing of air or gas into the respective bellows through the various inlets and fluid paths described in detail above.

In a specific embodiment of the invention, the compressible ventilation reservoir(s) are positioned between the centre of rotation of footplate 602 and second end 612, while a resilient member (such as for example a spring) is positioned between the centre of rotation of footplate 602 and first end 610. The resilient member is configured and positioned such that it urges footplate 602 from the first position to the second position. In operation of this embodiment, footplate 602 is urged towards its first position by a force applied by an operator or care provider, causing the resilient member to resiliently deform. When the operator or care provider stops applying force on footplate 602, the resilient member moves towards its natural non-deformed state, and in doing so, urges footplate 602 back from the first position to the second position. Movement of footplate 602 from the first position to the second position causes compression of the compressible ventilation reservoir(s) located between the centre of rotation of footplate 602 and second end 610, thereby triggering the pedal ventilation stroke—and driving air through the airway interface. Since in this embodiment, the ventilation stroke is triggered by action of a resilient member, the force triggering the ventilation stroke remains constant in each ventilation stroke—thereby minimizing the risk of damage to a subject's airways or lungs caused by inadvertent over forceful triggering of the ventilation stroke.

It would be understood in all of the above embodiments, that the compressible reservoirs used as ventilation and suction pumps may be manufactured using resiliently deformable material such as rubber, silicone or plastic materials. The material of the compressible reservoirs may be selected to provide appropriate resilient properties so that (i) the compressible reservoirs cannot be unintentionally compressed and (ii) so that, in response to removal of compressive forces on the compressible reservoir(s), the compressed compressible reservoir(s) return to an expanded state with minimum delay.

In an embodiment of the invention, one or more compressible reservoirs may include a spring or other resilient member disposed therein, which spring or other resilient member is positioned to aid the compressible reservoir in regaining its expanded configuration.

In another embodiment of the invention the compressible reservoirs are made of non resilient material and are made to re-expand with the help of a resilient member which is mechanically coupled to the compressible reservoir by disposing the said resilient member inside the compressible reservoir or with the resilient member being placed outside the compressible reservoir but coupled by attachment of its ends to the ends of the compressible reservoir.

In another embodiment the compressible reservoirs are neither resilient nor are coupled with a resilient member, and instead, after having been compressed the compressible reservoir(s) are reinflated using a continuous flow from an air compressor or from a compressed air source such as a cylinder or a piped system from hospital central supply. Such arrangement is used in conjunction with an adjustable pressure limiting valve close to the patient valve. In such an arrangement because there is a continuous flow of air from the resuscitator to the patient, a non return valve may not be required.

In another embodiment of the invention, at least a first surface region of a compressible reservoir housed within pedal 306 may be disengageably or permanently affixed to hub 706, while at least a second surface region of the compressible reservoir (which second surface region of the compressible reservoir is preferably located at an opposite ends of the compressible reservoir relative to the first surface region) may be disengageably or permanently affixed to footplate 602. This arrangement ensures that as footplate 602 is urged away from base 604, the first and second regions of the compressible reservoir are drawn away from each other, thereby forcing the compressible reservoir from a compressed state to an expanded state.

In a specific embodiment of the invention, the second surface region of the compressible reservoir may be disengageably coupled to the selected region of footplate 602 by one or more fasteners, which may include clasps, buttons, screws, rivets, protrusions, magnets, snap fit flanges or combinations thereof.

In an embodiment of the invention, pedal 306 is configured such that, when base 604 is placed on a flat surface, the perpendicular distance between the centre of rotation (about which footplate 602 moves between its first position and its second position) of pedal 306, and said flat surface is between 27 mm and 32 mm, and preferably between 30 mm and 32 mm.

In another embodiment, pedal 306 may be configured such that, when base 604 is placed on a flat surface, the perpendicular distance between the centre of rotation (about which footplate 602 moves between its first position and its second position) of pedal 306, and an outer surface of footplate 602 is between 24 mm and 29 mm, and preferably between 27 mm and 29 mm.

In another embodiment, pedal 306 may be configured such that, when base 604 is placed on a flat surface, the perpendicular distance between an outer surface of footplate 602 and the flat surface, measured along an axis passing through the centre of rotation of footplate 602, is between 51 mm and 61 mm, and preferably between 57 mm and 61 mm.

In an embodiment of the invention, pedal 306 may be configured such that the maximum possible angular rotation about the centre of rotation (as the pedal moves between its first position and its second position) is less than 14° and preferably between 10° and 14°.

In an embodiment of the invention, pedal 306 is configured such that a ratio of (i) the distance between the centre of rotation of said pedal and second end 612 (x) to (ii) the distance between the centre of rotation of said pedal and first end 610 (y) is a value falling between 1:2 and 2:7 (x:y) and in an embodiment is between 22:78 and 26:74 (x:y).

In an embodiment of the invention, pedal 306 is configured such that a force of 100 newton or more is required to move footplate 602 from a first position to a second position or from a second position to a first position.

In an embodiment of the invention, pedal 306 is configured such that a force of 100 to 150 Newton is required to move footplate 602 from a first position to a second position or from a second position to a first position.

Ensuring that the force required to move the footplate remains within the above ranges ensures a proper balance between applied force and resistance offered, which makes it significantly easier to finely regulate the extent of compression. This also helps maintain postural balance of the operator and reduces fatigue caused by effort of finely regulating movement conducted by muscles designed for coarse movement (e.g. the gastrocnemius muscles).

The present invention additionally provides improvements to pressure relief valves (for example pressure relief valve 412 illustrated in FIG. 4B) incorporated within airway interfaces. It has been discovered that prior art pressure relief valves are only effective in preventing overpressure conditions to the extent that the rate of air inflow (i.e. air flow through the airway interface 302 through upstream first end 402 towards downstream second end 404) is less than the maximum rate of escape outflow (i.e. air flow permitted to escape out of the pressure relief valve, for example through openings 424 in cap 426). In the event the maximum rate of escape outflow is less than the rate of air inflow (for example, where the ventilation stroke is triggered by application of excessive force on pedal 306 (or excessive or excessively fast compression of the air reservoir by hand in case of prior art), the pressure relief valve is unable to vent sufficient amounts of air, leading to an overpressure situation which can potentially cause airway or lung trauma to the subject.

The present invention improves existing pressure relief valve mechanisms by introducing an air flow regulation mechanism, which ensures that the maximum rate of escape outflow from the pressure relief valve is always equal to or exceeds the rate of air inflow into the segment of the airflow circuit containing the pressure relief valve. The air flow regulation mechanism of the present invention achieves this objective by implementing an air flow regulator within the fluid path connecting the ventilation pump or ventilation bellows and the airway interface, which air flow regulator may be located at any point between a ventilation outlet 804 of the ventilation pump or ventilation bellows and the pressure relief valve 412 located within the airway interface 302. The air flow regulator ensures that the rate of airflow within airway interface 302 is at all times less than or equal to the maximum rate of escape outflow (i.e. air flow permitted to escape out of the pressure relief valve) of the pressure valve—especially under conditions of pressure and flow that can be encountered in the context of resuscitation of human subjects by human operators.

In an embodiment of the invention, the air flow regulator achieves this by ensuring that the minimum cross section of the fluid path that connects the source of ventilation gases (example, ventilation pump compressible ventilation reservoir) and the pressure release valve is less than or equal to the area available to vent (or allow escape of) air or ventilation gases from the release valve into the atmosphere (for example, the cumulative cross-sectional area provided by vent openings 424 in cap 426 of pressure release valve 412).

In an embodiment of the invention, the air flow regulator may comprise an obstruction within the fluid path connecting the source of ventilation gases to the airway interface, which obstruction reduces the cross-section of the fluid path to an area less than the cumulative maximum area available for venting ventilation gases from the pressure relief valve to the atmosphere.

In a preferred embodiment, the air flow regulator may comprise a circular occluder (or washer) positioned within said fluid path, having a lumen that permits passage of ventilation gases therethrough—wherein the area of the lumen at its narrowest point is less than or equal to the cumulative maximum area available for venting ventilation gases from the pressure relief valve to the atmosphere.

EXEMPLARY EMBODIMENTS

In an embodiment of the invention, a conduit carrying air from the foot pedal to the airway interface has an expansile segment located on the fluid path. This expansile segment serves as an indicator of rate of airflow and airflow pressure during a ventilation stroke (i.e. the rate and extent of inflation of said expansile segment provides a visual indicator of rate of pressure of airflow delivery.

An expansile segment may additionally serve as a device for providing positive end exoiratory pressure, wherein during a ventilation stroke (i.e. in response to compression of a ventilation reservoir), the expansile segment is forced into an expanded state by air entering said segment under pressure. During the recovery stroke (i.e. as the ventilation reservoir is recovering to its uncompressed state and is therefore not delivering air to an airway interface), resilient properties of the expansile segment cause said segment to regain its original non-inflated state by forcing air out of the expansile segment. Said air forced out of the expansile segment creates positive pressure applied to a subject's airway while the subject is exhaling—which is medically desirable.

The expansile segment may be a resilient balloon or other reservoir made of silicone or similar material having resilient properties, the resilience of which is chosen such that a minimum air pressure P may be required to cause measurable expansion. Said air pressure P may in an embodiment comprise air pressure at which pressure delivery by the device is intended to be limited.

A specific embodiment of the foot operated pedal is designed in a manner that the active stroke (ventilation stroke) is actuated by the heel of the operator instead of the fore-foot. In an embodiment, the position of the pedal is horizontal in the resting state and goes down by a specific angle below the horizontal to reach the first position (at the end of the ventilation stroke).

In yet another embodiment, the device includes a platform for the operator to place the resting foot on (and thus stand at a height) that is equal to the lowest point on the pedal top surface. This makes operation more ergonomic, as now the height by which the operator has to keep the active foot raised is effectively zero.

In an embodiment, the invention comprises a foot operated resuscitator (FOR) where the functional components live inside a thick openable outer-shell. In an embodiment, the foot operated resuscitator may permit internal components to be disassembled for mechanical cleaning and disinfection/sterilization. The foot operated resuscitator may include a common outer casing housing a resuscitator as well as a suction device.

The invention additionally provides a foot operated resuscitator where a high degree of force is required to compress the air reservoir, in order to enable greater force feedback and more controlled compression by larger muscle groups instead of the hand. These larger muscle groups may include muscles of lower leg, muscles of lower limb or foot muscles.

In an embodiment, the foot operated device may be configured to support the weight of the operator using an axis at the junction of anterior $3/4^{ths}$ and posterior $1/4^{th}$ allowing for an ergonomic action cycle and fatigue free operation.

In an embodiment of the foot operated resuscitator, the action stroke such as compression by foot leads to storage of energy in a mechanical or electronic system which later releases (either instantly or after a delay) and such release causes the actual compression of an air reservoir leading to propulsion of air or gas mixture for positive pressure ventilation.

The invention may additionally include a resuscitation device where, air or other gas mixture is introduced in a reservoir under a certain positive pressure using any means, including by way of any of the embodiments described herein—the build up of positive pressure in the reservoir can be configured to ensure a steady and continuous release of air from the reservoir to the airway interface, using any one of a variety of mechanisms that would be apparent to the skilled person. For delivery of positive pressure ventilation to a patient, this reservoir may be connected to a system of conduits connected to an airway interface device such as mask, endotracheal tube or nasal cannula and the periodic delivery of positive pressure to the patient's airway is actuated by a foot operated device distal to the reservoir. This ensures that the foot is only acting as an actuator and the pressure is regulated by setting the rate of efflux from the cylinder and with the help of valve proximal and distal to the foot operated switch. In an embodiment of the invention, a control (such as for example, a switch, solenoid, valve, pedal or other toggle mechanism capable of switching between two or more states) may be used to vary the rate and periodicity of airflow delivery from the reservoir to the airway interface (for example, to achieve any one or more of ventilation arrangements, bi-level positive airway pressure arrangements, or continuous positive airway pressure arrangements).

The invention additionally presents an arrangement where a large reservoir of air is created through a cylinder and piston arrangement, and a constant force is applied to the piston, for instance by placing a weight on top of the piston on a vertical cylinder. Such force builds up a pressure in the cylinder, and such pressure propels air out of this reservoir at a constant rate. This rate is modulated by applying a resistance to the efflux orifice of the cylinder. This air coming out of the cylinder is thereafter used for delivering positive pressure ventilation via a system of conduits and airway interface to the patient. The weight on the piston may be applied by making the operator stand on the piston.

It has additionally been found that higher than optimal airflows are often generated (intentionally or unintentionally) during the use of manually powered pressure generators such as compressible air reservoirs compressed by foot hand or any other body part. Higher than optimal airflows put the patient at the risk of trauma from excessive pressure, volume or flow (known as Barotrauma, Volutrauma and Rheotrauma respectively). Also, a patient's own airways apply a certain resistance to airflow, which is directly proportional to the rate at which air flows through them. Thus the higher the rate of airflow a resuscitation device delivers, the greater is the pressure drop through the airways. This leads to inadequate inflation pressure available at the alveoli (respiring region of the lung). Inadequate pressure leads to inadequate expansion of the lung (and in case of newborn infants, failure to expand fluid filled, poorly complaint lung segments which have poor compliance.) This leads to poor ventilation and attendant risks and ill effects.

Because, resuscitation is nearly always carried out under tense conditions, it is common and natural tendency among operators to press the air reservoir forcefully and rapidly leading to high flow rates and the above mentioned ill effects. In addition to what is mentioned above, another way in which high flow-rates lead to poor ventilation is the following: high flowrates lead to higher resistance being offered to airflow by patient airways and consequently to a faster build up of higher pressures in the air circuit between pressure release valve and patient airways. This leads to early opening of the pressure release valve and escape of significant volumes of air through the pressure release valve orifice. High flow also means faster escape of air through the open release valve orifice. Given the limited amount of air available in the pressure generating reservoir, this loss of air volume means that lesser volume is now available for ventilation of the patient's lungs—leading to inadequate ventilation.

When such poor ventilation is noticed by the operator, in the form of inadequate chest rise, there is a tendency to squeeze the air reservoir (by hand, foot or other body part) more forcefully and rapidly—leading to higher airflows. This in turn lead to even higher pressure drop through the airways (causing inadequate inflation pressures in the ventilating region, and larger volumes being lost via pressure release valve) and a vicious cycle is set up For the above reasons, while delivering manual positive pressure ventilation, longer inspiratory duration (with sustained pressure, prolonged inspiratory time) is recommended as opposed to short bursts of high pressure and high flow.

All prior art manual resuscitators are designed to be very easy to compress (to avoid fatigue). As such all prior art manual resuscitators suffer from a high chance causing high flow rates and the attendant ill effects mentioned above.

In an embodiment of the current invention, an adjustable (or non-adjustable) resistance or occlude to airflow is inserted in the air-path between the pressure generating component and pressure release valve. The area of the orifice within the resistance or occluder is determined in a manner that ensures that the rate of flux of air or mixture of gases for ventilation occurs at a rate F, where F is the rate of efflux expected to occur from the pressure release valve opening at the given pressure and flow rate. In an embodiment for instance, the orifice is designed in a way to ensure that the maximum possible flow rate through the pressure release valve under operating conditions of the resuscitator is also the maximum possible rate at which the resistor allows air to pass through it. Additionally, providing an adjustable or variable resistance to airflow ensures that by reducing the area available for passage of air between a ventilation reservoir and airway interface, the resistance significantly reduces or entirely eliminates spiking of peak airflow and/or peak air pressure through the airway interface, and enables sustained air pressures and airflows over the duration of the ventilation stroke (or breath delivery), which has been found to be advantageous.

However, adding a limitation to flow of air through the resistor may prevent generation of high flow rates that may be specifically required in certain conditions such as when high inflating pressures are actually required. For such situations, this resistor component is made adjustable and the operator can reduce the resistance as per requirement.

Such resistor component can be applied anywhere between pressure generating component and pressure release valve. When applied close to the pressure generating reservoir, it offers the benefit of closer correlation between rate of compression and rate of flow generation. When applied close to the pressure release valve, it offers the benefit of easy adjustability by the operator.

In another embodiment, a constant or adjustable resistance is added between the pressure release valve and the non-return valve. When this resistance is increased, for instance by narrowing the orifice, a higher pressure is built up proximal to resistance, per unit pressure applied. This higher pressure leads to opening of the release valve and release of air/gas mixture from the pressure release valve. Now only the remaining amount of air/gas mixture is available for entering into the patient's lung. The adjustable resistance may have a knob or slider other mechanical user interface component using which its resistance can be adjusted by the user during operation. In an embodiment, the constant or adjustable resistance prevents flow rates from rising above f, wherein f is a rate that is high enough to ensure adequate and timely ventilation while avoiding unduly rapid build up of pressure that would otherwise lead to premature opening of the pressure release valve or that could cause generation of unduly high airway resistance from patient airways. In an embodiment, the constant or adjustable resistance is a resistance that causes a pressure drop of between 30 cm and 50 cm of $H_2O$ at 10 litres/minute.

In another embodiment, a leaking orifice is provided in the segment of the patient interface located at any of the following locations: (i) anywhere between the pressure generating component and the pressure release valve (ii) anywhere between the pressure release valve and the non-return patient valve (iii) anywhere in the patient interface after the non return valve (iv) anywhere in the mask.

This leaking orifice is left adjusted by default to a minimum or no leak setting in certain conditions. When it is required to finely regulate the volume delivered to the patient, such leak can be used to release excess air out of the artificial breathing circuit. Such arrangement is especially helpful in conjunction of the pedal arrangement where compression of the air reservoir is driven by a resilient spring instead of a direct manual force. Since such force may be constant, an adjustment is required to account for varying needs of patients. Such adjustment is may be effected by moving a knob or a slider the adjusts the diameter and hence the percentage of total air propelled leaking out of the said orifice, which in turn determines the volume of air actually being delivered to the patients airways—whether through an invasive interface such as endotracheal tube or through any other non-invasive or semi-invasive interface such as face mask or laryngeal mask airway.

In another embodiment, the exhaled air, which is released from the undersurface of the patient interface is collected using a receptacle and routed through a narrow tube (NT) fitted with a whistle. Such whistle creates a sound whenever air travels through it. This informs the operator that the air has been delivered to the patient as the patient is exhaling. The whistle is designed in a way that a sound is generated from it even at very low flows. The duration of the sound gives an estimate of the amount of air exhaled and therefore the amount of air inhaled. In another embodiment, the frequency of the sound created is directly proportional to flow rate and this also gives an estimate of the amount of air being exhaled and hence inhaled.

In another embodiment instead of a whistle, a mechanical module for flow detection is attached, such as a mechanical flow meter, to inform the operator of the expiratory flow and hence an estimate of exhaled volume and hence inhaled volume.

In another embodiment, the mechanical flowmeter is replaced with a cylindrical or toroidal track with a ball or piston having an interfering fit. When exhaled air enters this track, it pushes the ball through a distance commensurate with the exhaled volume entering the track. A channel is created to allow entry of positive pressure breaths being delivered in the next cycle to enter the toroidal track from the opposite end—which pushes the piston/ball to its original zero position.

In another embodiment, a balloon like structure is attached to the point NT. Exhaled air serves to inflate the balloon, which has a narrow hole. The balloon fills up with exhaled air and slowly empties through the hole. The size to which the balloon inflates gives an estimate of the amount of air inhaled.

In an embodiment, an expansile structure such as a balloon or a transparent cylinder with a piston is attached to the point where a manometer is required to be attached. This component is designed so as to require a similar amount of pressure per unit volume expansion as does the lung of the patient in question. Approximate ranges of expansion are known for different age groups. As such, expansion of this balloon will also give an estimate of the volume of air actually delivered to the lung, to the extent that the compliance of this structure matches the compliance of the patient's lung. Such an invention would be of special use for infants and children where the lung volume is much smaller in comparison of the volume of air in the reservoir available for delivery into the lung for ventilation.

In an embodiment, the effective diameter of the orifice in the pressure release valve is altered. A larger orifice leads to a lower release pressure, beyond which air/gas mixture starts bleeding out, limiting the pressure in the respiration system.

In another embodiment, the biasing of the spring in the pressure release valve can be altered. For instance if a spring is urged onto the component that covers the bleeding orifice, greater pressure would be required to lift up the spring and as such the limiting pressure would be at a higher value than the original pressure at which the pressure release valve inherently releases air.

It would be understood that the examples and embodiments discussed in the present specification are illustrative only. Those skilled in the art would immediately appreciate that various modifications in form and detail may be made without departing from or offending the spirit and scope of the invention as defined by the appended claims.

We claim:

1. A resuscitation device comprising:
   a set of ventilation reservoirs, comprising at least one compressible fluid reservoir, wherein the set of ventilation reservoirs includes:
   at least a first fluid inlet that enables fluid to be drawn into the set of ventilation reservoirs; and
   at least a first fluid outlet configured for coupling with an airway interface through a ventilation conduit, wherein the ventilation conduit is configured to provide fluid passageway between the set of ventilation reservoirs and the airway interface; and
   a set of suction reservoirs, comprising at least one compressible fluid reservoir, wherein the set of suction reservoirs includes:
   at least a second fluid inlet configured for coupling with a suction conduit; and
   at least a second fluid outlet configured to enable fluid to be expelled from the set of suction reservoirs;
   a housing configured to accommodate the plurality of compressible fluid reservoirs, the housing comprising a base;
   a footplate comprising a first end and a second end;
   a pivot coupling the footplate to the housing, such that the footplate is pivotable about a center of rotation, between:
   a first position where the first end of the footplate is urged towards the base and the second end of the footplate is urged away from the base; and a second position where the first end of the footplate is urged away from the base and the second end of the footplate is urged towards the base;

wherein the set of ventilation reservoirs and the set of suction reservoirs are disposed between the base and the foot plate;

wherein the set of ventilation reservoirs and the set of suction reservoirs are positioned such that movement of the footplate between one of the first and second positions and the other of said first and second positions, compresses one or more of the compressible fluid reservoirs; and wherein a fluid space within the set of ventilation reservoirs is isolated from the fluid space within the set of suction reservoirs.

2. The resuscitation device as claimed in claim 1, wherein the set of ventilation reservoirs are positioned between the center of rotation of the footplate and the first end of the footplate, and the set of suction reservoirs are positioned between the center of rotation of the footplate and the second end of the footplate.

3. The resuscitation device as claimed in claim 1, wherein at least one compressible fluid reservoir within the set of ventilation reservoirs or the set of suction reservoirs includes a resilient member disposed therein, and which resilient member is configured to urge the compressible fluid reservoir from a compressed configuration towards an expanded configuration.

4. The resuscitation device as claimed in claim 1, wherein a perpendicular distance between the footplate and a lower surface of the base along a perpendicular axis passing through the center of rotation is between 51 mm and 61 mm.

5. The resuscitation device as claimed in claim 1, wherein a maximum angular deviation from a horizontal plane that is capable of being achieved by the footplate in pivoting about the center of rotation, is less than 14 degrees.

6. The resuscitation device as claimed in claim 1, wherein a ratio of (i) the distance between the center of rotation and the second end of the footplate to (ii) the distance between the center of rotation and the first end of the footplate is between 1:2 and 2:7.

7. The resuscitation device as claimed in claim 1, configured such that force of above 100 Newton is required to move the footplate between one of the first position and the second position, and the other of the first position and the second position.

8. The resuscitation device as claimed in claim 1, further comprising a hub disposed within the housing, said hub comprising:
 a ventilation conduit interface configured to engage with the ventilation conduit;
 a suction conduit interface configured to engage with the suction conduit;
 a plurality of reservoir mounts, wherein each reservoir mount provides a compressible fluid reservoir interface for mounting a compressible fluid reservoir such that each compressible fluid reservoir is in fluid communication with one of the ventilation conduit and the suction conduit; and
 a plurality of conduit passageways connecting the reservoir mounts and configured such that:
  each compressible fluid reservoir within the set of ventilation reservoirs is in fluid communication with the other compressible fluid reservoirs within the set of ventilation reservoirs, and with the first fluid inlet and the first fluid outlet;
  each compressible fluid reservoir within the set of suction reservoirs is in fluid communication with the other compressible fluid reservoirs within the set of suction reservoirs, and with the second fluid inlet and the second fluid outlet; and
 the fluid space within the set of ventilation reservoirs is isolated from the fluid space within the set of suction reservoirs.

9. The resuscitation device as claimed in claim 1, comprising a safety apparatus for controlling pressure of ventilation gas delivered through the airway interface, the safety apparatus comprising:
 a pressure release valve provided on a fluid passageway connecting the set of ventilation reservoirs and the airway interface, configured to respond to an abnormal pressure event by releasing ventilation gas through one or more release orifices into the atmosphere; and
 a fluid passageway constriction disposed in a fluid passageway between the set of ventilation reservoirs and the pressure release valve, wherein the fluid passageway constriction is configured such that a maximum rate of airflow permitted through said constriction is less than or equal to a maximum rate of airflow permitted through said one or more release orifices.

10. The resuscitation device as claimed in claim 9, wherein the fluid passageway constriction comprises a removable occluder disposed in the fluid passageway between the set of ventilation reservoirs and the pressure release valve, wherein the occluder is configured to partially obstruct the fluid passageway such that at its narrowest dimension a maximum rate of airflow permitted through said occluder is less than or equal to the maximum rate of airflow permitted through said one or more release orifices.

11. The resuscitation device as claimed in claim 1, where the pivot coupling comprises an L-shaped rocker having a first end and a second end.

12. The resuscitation device as claimed in claim 1, comprising a resilient member positioned between the center of rotation and one of the first end and the second end of the footplate and configured to urge the footplate away from the base of the housing, wherein the resilient member is configured such that resilient force exerted by the resilient member triggers compression of the plurality of compressible fluid reservoirs.

13. The resuscitation device as claimed in claim 1, comprising a fluid passageway resistance disposed in a fluid passageway between the set of ventilation reservoirs and the airway interface, wherein the fluid passageway resistance is a resistance that causes a pressure drop of 30 to 50 cm $H_2O$ at a flow rate of 10 litres/minute.

14. The resuscitation device as claimed in claim 1, comprising a positive end expiratory pressure device, said positive end expiratory pressure device comprising a resilient expansile segment disposed on a fluid passageway between the set of ventilation reservoirs and the airway interface, wherein the expansile segment is configured such that (i) responsive to a ventilation stroke the expansile segment is forced into an expanded state by air entering the expansile segment under pressure and (ii) responsive to a recovery stroke, the expansile segment contracts, wherein contraction of the expansile segment creates positive pressure on a subject's airway during exhalation.

15. The resuscitation device as claimed in claim 14, wherein the expansile segment is disposed on the fluid passageway and incorporates (i) a one-way inlet valve and (ii) a high resistance outlet orifice, configured such that a rate of inflow into the expansile segment is higher than a rate of outflow therefrom.

* * * * *